(12) United States Patent
Sato

(10) Patent No.: US 8,206,286 B2
(45) Date of Patent: Jun. 26, 2012

(54) TIGHTENING STRING FOR AN ENDOSCOPE, OUTER COVER SECURING METHOD, FLEXIBLE TUBE FOR AN ENDOSCOPE, AND AN ENDOSCOPE

(75) Inventor: Yasuyuki Sato, Saitama (JP)

(73) Assignee: Hoya Corporation, Tokyo (JP)

( * ) Notice: Subject to any disclaimer, the term of this patent is extended or adjusted under 35 U.S.C. 154(b) by 928 days.

(21) Appl. No.: 11/387,676

(22) Filed: Mar. 24, 2006

(65) Prior Publication Data

US 2006/0258911 A1 Nov. 16, 2006

(30) Foreign Application Priority Data

Mar. 25, 2005 (JP) .................................. 2005-089488
Jun. 9, 2005 (JP) .................................. 2005-169686

(51) Int. Cl.
*A61B 1/00* (2006.01)
*D02G 3/00* (2006.01)
(52) U.S. Cl. .................. 600/139; 600/140; 428/375
(58) Field of Classification Search .................... 57/234, 57/210, 230, 232, 236, 241; 600/125, 130, 600/139–142; 428/114, 222
See application file for complete search history.

(56) References Cited

U.S. PATENT DOCUMENTS

| | | | | |
|---|---|---|---|---|
| 3,599,679 A | * | 8/1971 | Carter | 139/420 R |
| 3,625,809 A | * | 12/1971 | Caroselli et al. | 428/222 |
| 3,911,785 A | * | 10/1975 | Hood | 87/1 |
| 4,347,837 A | * | 9/1982 | Hosono | 600/139 |
| 4,548,866 A | * | 10/1985 | Cordova et al. | 428/398 |
| 4,805,596 A | * | 2/1989 | Hatori | 600/139 |
| 5,947,979 A | | 9/1999 | Ouchi et al. | |
| 6,206,824 B1 | | 3/2001 | Ohara et al. | |
| 6,527,706 B2 | * | 3/2003 | Ide | 600/142 |
| 6,565,505 B2 | * | 5/2003 | Ishibiki | 600/133 |
| 6,814,697 B2 | | 11/2004 | Ouchi | |

(Continued)

FOREIGN PATENT DOCUMENTS

JP 2-175938 7/1990
(Continued)

OTHER PUBLICATIONS

Japan Office action, dated Apr. 26, 2011 along with an english translation thereof.

(Continued)

*Primary Examiner* — Matthew J Kasztejna
*Assistant Examiner* — Ryan Henderson
(74) *Attorney, Agent, or Firm* — Greenblum & Bernstein, P.L.C.

(57) ABSTRACT

A tightening string is used in an endoscope for firmly securing an outer cover of a flexible tube of the endoscope onto an internal member disposed inside the outer cover. The tightening string is comprised of a filament assembly formed by bundling a plurality of filaments made of a synthetic resin. The invention also provides an outer cover securing method, a flexible tube for an endoscope, and an endoscope equipped with the flexible tube. Alternatively, the filament assembly may include a first filament having an elongation ratio at room temperature of greater than 10% and a second filament having a elongation ratio at room temperature of equal to or lower than 10%, in which the filament assembly is formed by twisting the first and second filaments. An outer cover securing method using the tightening string, a flexible tube for an endoscope equipped with the thus secured outer cover, and an endoscope equipped with the flexible tube are also provided.

9 Claims, 11 Drawing Sheets

U.S. PATENT DOCUMENTS

| | | |
|---|---|---|
| 7,011,627 B2 | 3/2006 | Abe |
| 2003/0236553 A1* | 12/2003 | Knudsen ........................ 606/228 |
| 2004/0058152 A1* | 3/2004 | Tokarsky et al. .............. 428/373 |
| 2005/0125036 A1* | 6/2005 | Roby ............................. 606/228 |
| 2005/0209508 A1* | 9/2005 | Aono et al. .................... 600/140 |
| 2006/0048497 A1* | 3/2006 | Bloch .............................. 57/230 |

FOREIGN PATENT DOCUMENTS

| | | |
|---|---|---|
| JP | 02-175938 | 7/1990 |
| JP | 5-277061 | 10/1993 |
| JP | 7-34344 | 2/1995 |
| JP | 8-56897 | 3/1996 |
| JP | 8-112229 | 5/1996 |
| JP | 10-099263 | 4/1998 |
| JP | 2001-137179 | 5/2001 |
| JP | 2002-034900 | 2/2002 |
| JP | 2002-34900 | 2/2002 |
| JP | 2002-155438 | 5/2002 |
| JP | 2002-194635 | 7/2002 |
| JP | 2004-166840 | 6/2004 |

OTHER PUBLICATIONS

Japan Office action, dated Nov. 24, 2010 along with an english translation thereof.
Japan Office action, dated Dec. 7, 2010 along with an english translation thereof.
Japan Office action, dated Feb. 8, 2011 along with an english translation thereof.
Japan Office action, dated Mar. 1, 2011 along with an english translation thereof.
English Language Abstract of JP 5-277061.
English Language Abstract of JP 2002-034900.
U.S. Appl. No. 09/775,629 to T. Ouchi, filed Feb. 5, 2001.

* cited by examiner

TIGHTENING STRING FOR AN ENDOSCOPE, OUTER COVER SECURING METHOD, FLEXIBLE TUBE FOR AN ENDOSCOPE, AND AN ENDOSCOPE

BACKGROUND OF THE INVENTION

1. Field of the Invention

The present invention relates to a tightening string for an endoscope, an outer cover securing method, a flexible tube for an endoscope, and an endoscope, and more specifically relates to a tightening string for use in an endoscope for securing an outer cover of a flexible tube of the endoscope onto a core member of the flexible tube disposed inside the outer cover, an outer cover securing method using the tightening string, a flexible tube for an endoscope equipped with the thus secured outer cover, and an endoscope equipped with the flexible tube.

2. Description of the Related Art

In the medical fields, an endoscope is used for examining and diagnosing a gastrointestinal tract or the like of a patient.

Such an endoscope includes an insertion section flexible tube which is to be inserted into a body cavity of a patient, an operating section for performing operations of the insertion section flexible tube, a connecting section flexible tube connected to the operating section, and a light source plug provided on the tip end of the connecting section flexible tube.

The insertion section flexible tube (hereinafter, simply referred to as "flexible tube") has an elongated flexible tubular portion and a bendable portion coupled to the tip end of the flexible tubular portion in a bendable manner. The body cavity can be observed in all directions by rotating the flexible tube and, at the same time, bending the bendable portion of the flexible tube appropriately.

In general, the flexible tubular portion and the bendable portion are respectively comprised of a core member and an outer cover having flexibility and covering the core member. In such an endoscope, the flexible tubular portion and the bendable portion are coupled together in the following manner (for example, see JP-A No. 5-277061).

First, the core members of the flexible tubular portion and the bendable portion are joined together at their end portions, after which the joined part is covered with an outer cover of the bendable portion, and then the end of an outer cover of the flexible tube is brought into contact with the end of the outer cover of the bendable portion.

Then, the outer cover of the flexible tubular portion and the outer cover of the bendable portion are respectively tightened by a string at the opposite sides of the boundary section therebetween, and then an adhesive agent is applied over the string.

By applying the adhesive agent over the tightening string in this manner, the string is secured to the outer cover of the flexible tube and the outer cover of the bendable portion.

In the meantime, an endoscope is subject to cleansing, disinfecting and sterilizing every time upon its use. From the view point of improving safety, stronger treatment agents and methods have been employed in recent years in the process of sterilization.

However, if the strong sterilization treatment is carried out for the endoscope, it causes a problem in that the adhesive agent becomes deteriorated and this causes a brittle fracture in the hardened adhesive or a reduction of bonding strength, thereby loosening the string, which results in decrease in the liquid-tightness at the joining section. In the event that such a problem occurs, a liquid such as a disinfecting liquid or the like may be infiltrated into the inside of the endoscope through the joining section. This involves a risk that the endoscope is out of order.

Further, depending on the property of the string used, there is a case that the outer cover is damaged. The damaged outer cover causes a problem in that the liquid-tightness of the flexible tubular portion and the bendable portion is lowered, and this also involves a risk that the endoscope fails to operate properly.

Furthermore, in order to secure the outer cover to the core member more firmly with suppressing the burden to a patient to which an endoscope is to be inserted as lower as possible, there is a demand that a string which is more suitable for a tightening string for an endoscope should be developed.

SUMMARY OF THE INVENTION

In view of the above problems, an object of the present invention is to provide a tightening string for use in an endoscope capable of firmly securing an outer cover of a flexible tube of the endoscope onto an internal member disposed inside the outer cover.

Further, another object of the present invention is to provide an outer cover securing method for firmly securing an outer cover of a flexible tube of the endoscope onto an internal member disposed inside the outer cover through the use of such a tightening string for an endoscope.

Furthermore, other object of the present invention is to provide a flexible tube for an endoscope having an outer cover secured by such an outer cover securing method and capable of maintaining an enhanced liquid-tightness for a prolonged period of time even when a disinfecting and sterilizing treatment is carried out repeatedly.

Moreover, yet other object of the present invention is to provide an endoscope equipped with such a flexible tube for an endoscope.

In order to achieve the above object, one aspect of the present invention is directed to a tightening string for use in an endoscope for securing an outer cover of a flexible tube of the endoscope onto an internal member disposed inside the outer cover, wherein the tightening string is comprised of a filament assembly formed by bundling a plurality of filaments made of a synthetic resin.

According to the tightening string for use in an endoscope described above, it is possible to obtain a tightening string for use in an endoscope capable of firmly securing an outer cover of a flexible tube of the endoscope onto an internal member disposed inside the outer cover (hereinafter, the term "outer cover" is used as a meaning that includes an outer cover 32 of a flexible tubular portion 3 and an outer cover 42 of a bendable portion 4 on occasions).

In addition, since the filaments are composed of pliant and long fibers, the tightening string (filaments) for an endoscope is prevented from severing when wound around and tightened on the outer cover. As a result, when the tightening string for an endoscope has been covered with an adhesive agent, it is possible to avoid any protrusion of the ends of the filaments to the outside from the adhesive agent or any creation of a micro-asperity (fluff or fuzz) on the surface of the adhesive agent. Therefore, it is possible for the tightening string for an endoscope to secure the outer cover onto the core member reliably.

Further, in the tightening string for use in an endoscope described above, it is preferred that the filament assembly includes a filament twist obtained by twisting the plurality of filaments.

By virtue of this, alternating ridges-and-valleys (gaps) are periodically formed on the surface of the filament twist. An adhesive agent is spread into the ridges-and-valleys to thereby give birth to a stronger anchor effect with respect to the tightening string for an endoscope so that the tightening string can be bonded with greater adhesive strength. As a result, it is possible for the adhesive agent to surely secure the tightening string in place.

Further, in the tightening string for use in an endoscope described above, it is preferred that the filament assembly includes a plurality of the filament twists.

This provides to a stronger anchor effect with respect to the tightening string for an endoscope.

Further, in the tightening string for use in an endoscope described above, it is also preferred that the filament assembly is obtained by twisting the plurality of filament twists.

This creates a plurality of ridges-and-valleys on the surface of the filament assembly, thus making quite greater the surface area of the filament assembly. This enables an anchor effect to be exhibited particularly strongly, making it possible for the adhesive agent to reliably secure the tightening string for an endoscope in place. It is also possible to improve the mechanical strength of the tightening string for an endoscope itself.

Further, in the tightening string for use in an endoscope described above, it is also preferred that a relationship B/A is in the range of 2 to 30, where A denotes the outer diameter (mm) of each of the filaments and B represents the outer diameter (mm) of the filament assembly.

This creates an appropriate size of ridges-and-valleys on the region tightened by the tightening string for an endoscope. At the time of securing the tightening string with an adhesive agent, the adhesive agent is spread into the ridges-and-valleys by the capillary phenomenon. Thus, by the stronger anchor effect, the adhesive agent is bonded to the tightening string with greater adhesive strength. As a result, it is possible for the adhesive agent to reliably secure the tightening string in place.

Further, in the tightening string for use in an endoscope described above, it is also preferred that the filaments are bonded to one another at least partially along a longitudinal direction thereof.

This increases the tying force with which the filaments are bundled together. It is therefore possible for the tightening string for an endoscope to keep the outer cover in the secured condition for an extended period of time and in a stabilized manner.

Further, in the tightening string for use in an endoscope described above, it is preferred that the securing is conducted by heating.

This induces rearrangement of the inter-molecular bonds in the filaments, thus allowing the shape of the filaments to be stably kept in a twisted condition. Accordingly, the filaments are entwined with one another and can be at least partially fixed along a longitudinal direction thereof.

Furthermore, in the tightening string for use in an endoscope described above, it is also preferred that the synthetic resin has polar structures in its main chains and/or side chains.

This strengthens the interaction between polar structures and an adhesive agent and thus can enhance the bonding strength of the filaments to the adhesive agent.

In this case, it is preferred that the synthetic resin comprises, as the polar structures, at least one of —OH, —CHO, —NCO, —COOH, —O—, —CO—, —COO—, —CONH—, —CONHCO— and —NHCOO—.

These polar structures are contained in great quantity within a constituent material of the adhesive agent. Therefore, by permitting the main chains and/or side chains to contain the polar structures, it becomes possible to make greater the bonding strength between the filaments and the adhesive agent.

Furthermore, in the tightening string for use in an endoscope described above, it is also preferred that the synthetic resin has a melting point or softening point of 150° C. or higher.

This imparts sufficient durability to the tightening string for an endoscope against a disinfecting or sterilizing treatment conducted in an autoclave or the like under an elevated temperature. As a result, even though an endoscope is repeatedly subject to a sterilizing treatment (particularly, an autoclave sterilization), it is possible to keep high the liquid-tightness between a flexible tubular portion and a bendable portion for a prolonged period of time and in a surer manner.

Furthermore, in the tightening string for use in an endoscope described above, it is also preferred that each of the filaments has an elongation ratio (breaking elongation ratio) of greater than 10%.

This makes sure that the filaments are prevented from severing even in the case where the tightening string for an endoscope is given a shock accompanying, e.g., a suddenly acting heavy tensile force, or a thermal shock.

Further, in the tightening string for use in an endoscope according to the present invention, it is preferred that the filament assembly includes at least one first filament having an elongation ratio at room temperature of equal to or lower than 10% and at least one second filament having an elongation ratio at room temperature of higher than 10%, and the filament assembly is formed by twisting the first and second filaments.

According to the tightening string for use in an endoscope described above, it is possible to obtain a tightening string for use in an endoscope that can firmly secure the tubular outer cover onto the internal member disposed inside the outer cover without damaging the outer cover.

In the tightening string for use in an endoscope described above, it is preferred that the filament assembly includes a filament twist obtained by twisting the first and second filaments.

Such a tightening string makes it possible to firmly secure the outer cover onto the internal member.

Further, in the tightening string for use in an endoscope described above, it is also preferred that the filament assembly is obtained by twisting a plurality of the filament twists.

This makes it possible to create a stronger anchor effect between the adhesive agent and the tightening string.

Further, in the tightening string for use in an endoscope described above, it is also preferred that the filament assembly includes at least one first filament twist obtained by twisting a plurality of first filaments and at least one second filament twist obtained by twisting a plurality of second filaments.

Such a tightening string also makes it possible to firmly secure the outer cover onto the internal member.

In this case, it is preferred that the filament assembly is formed by twisting the first and second filament twists.

This also makes it possible to create a stronger anchor effect between the adhesive agent and the tightening string.

Further, in the tightening string for use in an endoscope described above, it is also preferred that the number of twisting of each of the filament twist, the first filament twist and the second filament twist is in the range of 700 to 1500 T/m.

Such a tightening string also makes it possible to firmly secure the outer cover onto the internal member. In addition, it is possible to create a stronger anchor effect between the adhesive agent and the tightening string.

Further, in the tightening string for use in an endoscope described above, it is preferred that the number of twisting of the filament assembly is in the range of 400 to 800 T/m.

Such a tightening string also makes it possible to firmly secure the outer cover onto the internal member. In addition, it is possible to create a stronger anchor effect between the adhesive agent and the tightening string.

Further, in the tightening string for use in an endoscope described above, it is preferred that in the case where the elongation ratio of the first filament at room temperature is defined as $S_1$ (%) and the elongation ratio of the second filament at room temperature is defined as $S_2$ (%), the value $S_1/S_2$ is in the range of 0.02 to 0.95.

This makes it possible to tighten the outer cover firmly with the tightening string while reliably preventing the outer cover from being damaged due to the tightening by exhibiting an appropriate elongation.

Further, in the tightening string for use in an endoscope described above, it is preferred that in the case where the cross-sectional area of the second filament is defined as A (mm$^2$) and the cross-sectional area of the filament assembly is defined as B (mm$^2$), the value A/B is in the range of 0.05 to 0.5.

This makes it possible to firmly tighten the outer cover with the first filaments having a relatively small elongation ratio and to prevent the outer cover from being damaged due to elongation of the second filament having a relatively large elongation ratio, and these synergistic effect becomes conspicuous.

Further, in the tightening string for use in an endoscope described above, it is also preferred that in the case where the outer diameter of the filament assembly is defined as C (mm) and an average thickness of the outer cover is defined as D (mm), the value C/D is in the range of 0.05 to 0.5.

This makes it possible to increase a burden on a patient by an increased diameter of the insertion section flexible tube due to the tightening string while the outer cover is reliably tightened by the tightening string.

Furthermore, in the tightening string for use in an endoscope described above, it is also preferred that the first filament is mainly formed of a polyarylate-based resin.

Since the polyarylate-based resin has an elongation ratio at room temperature of 10% or less and has excellent tensile strength, it is possible to obtain a tightening string for an endoscope which is difficult to sever and by which it is possible to tighten the outer cover firmly. Further, the polyarylate-based resin also has high elasticity. Therefore, by tightening the outer cover with tensioning the tightening string, the tightening string 9 is contracted after tightening it, and thus this provides a more firmly tightening state.

Furthermore, in the tightening string for use in an endoscope described above, it is also preferred that the second filament is mainly formed of a resin material or a metallic material.

This makes it possible to easily obtain the second filament having an elongation ratio at room temperature of 10% or higher.

In this case, it is preferred that the resin material contains as its main component at least one of polyamide and polyphenylene sulfide.

Since these resins have an elongation ratio at room temperature of 10% or higher, they have a sufficient tensile strength for tightening the outer cover reliably.

Further, in the above case, it is preferred the metallic material contains as its main component at least one of stainless steel and tungsten.

By using these metallic materials, it is possible to easily obtain a relatively fine filament having an elongation ratio at room temperature of 10% or higher though there is an exception depending on the shape thereof (e.g. the outer diameter of the filament) or the like. Further, since these metallic materials have an extremely high hardness, it is possible to prevent the tightening string from being severed due to wear caused by friction when tightening the outer cover.

Furthermore, in the tightening string for use in an endoscope described above, it is also preferred that the first and second filaments are bonded to one another at least portions thereof along a longitudinal direction thereof.

This increases the tying force with which the filaments are bundled together. It is therefore possible for the tightening string for an endoscope to keep the outer cover in the secured condition for an extended period of time and in a stabilized manner.

Furthermore, in the tightening string for use in an endoscope described above, it is also preferred that the constituent material of the first filament and each of the constituent material of the second filament has a melting point or softening point which is equal to or higher than 150° C.

This makes it possible for the tightening string to have sufficient resistance against a disinfecting or sterilizing treatment conducted in an autoclave or the like under an elevated temperature.

Another aspect of the present invention is directed to an outer cover securing method for securing an outer cover of a flexible tube of an endoscope onto an internal member disposed inside the outer cover, comprising the steps of:

a first step of disposing the internal member inside the outer cover;

a second step of tightening the outer cover from an outer surface thereof with the tightening string for an endoscope defined in claim 1; and a third step of securing the tightening string for an endoscope by covering the tightening string with an adhesive agent.

By using this securing method, it is possible to secure the outer cover onto the internal member disposed inside the outer cover firmly.

In the above securing method, it is preferred that the adhesive agent contains as its main component at least one of an epoxy-based adhesive agent, a urethane-based adhesive agent, an acryl-based adhesive agent and an ester-based adhesive agent.

These adhesive agents are relatively high in a chemical resistance and a heat resistance. Therefore, the adhesive agent is prevented from degeneration or degradation even in the case that the electronic endoscope is repeatedly subject to a disinfecting or sterilizing treatment. Owing to this, the tightening string can reliably keep the outer cover secured to the internal member. Further, it is also possible to maintain enhanced liquid-tightness between the flexible tubular portion and the bendable portion for a prolonged period of time.

Other aspect of the present invention is directed to a flexible tube for an endoscope, the flexible tube being adapted to be inserted into a body cavity of a patient, comprising:

a flexible tubular portion including a core member and an outer cover which covers an outer periphery of the core member, the flexible tubular portion having a tip end and a base end; and a bendable portion provided at the tip end of the flexible tubular portion and including a core member and an outer cover which covers an outer periphery of the core member, the bendable portion having a tip end and a base end, wherein an end portion of the outer cover of the bendable portion at the base end side thereof and an end portion of the outer cover of the flexible tubular portion positioned at the tip end side thereof are secured onto the core member of the bendable portion or the core member of the flexible tubular portion by mean of the tightening string for an endoscope defined in claim 1.

The other aspect of the present invention is also directed to a flexible tube for an endoscope, the flexible tube being adapted to be inserted into a body cavity of a patient, comprising:

a flexible tubular portion including a core member and an outer cover which covers an outer periphery of the core member, the flexible tubular portion having a tip end and a base end;

a bendable portion provided at the tip end of the flexible tubular portion and including a core member and an outer cover which covers an outer periphery of the core member, the bendable portion having a tip end and a base end; and a tightening string for securing an end portion of the outer cover of the bendable portion at the base end side thereof and an end portion of the outer cover of the flexible tubular portion at the tip end side thereof onto the core member of the bendable portion or the core member of the flexible tubular portion, wherein the tightening string is comprised of a filament assembly formed by bundling a plurality of filaments made of a synthetic resin.

These flexible tubes for an endoscope can maintain enhanced liquid-tightness between the flexible tubular portion and the bendable portion for a prolonged period of time even in the case that the electronic endoscope is repeatedly subject to a disinfecting or sterilizing treatment.

A still further aspect of the present invention is also directed to an endoscope equipped with the flexible tube for an endoscope as described above.

This makes it possible to obtain an endoscope whose outer cover is kept in a secured condition for an extended period of time and in a stabilized manner. Further, by using such an endoscope, it is possible to hold a burden on a patient as smaller as possible.

A still other aspect of the present invention is directed to a tightening string for use in an endoscope for securing an outer cover of a flexible tube of the endoscope onto an internal member disposed inside the outer cover, wherein the tightening string is comprised of a filament assembly which includes at least one first filament having an elongation ratio at room temperature of equal to or lower than 10% and at least one second filament having an elongation ratio at room temperature of higher than 10%, and the filament assembly is formed by twisting the first and second filaments.

These and other objects, structures and results of the present invention will be apparent more clearly when the following detailed description of the preferred embodiment is considered taken in conjunction with the appended drawings.

DETAILED DESCRIPTION OF THE PREFERRED EMBODIMENTS

In conjunction with preferred embodiments shown in the accompany drawings, a tightening string for an endoscope, an outer cover securing method, a flexible tube for an endoscope, and an endoscope according to the present invention will be described in detail hereinbelow.

Figure 1:
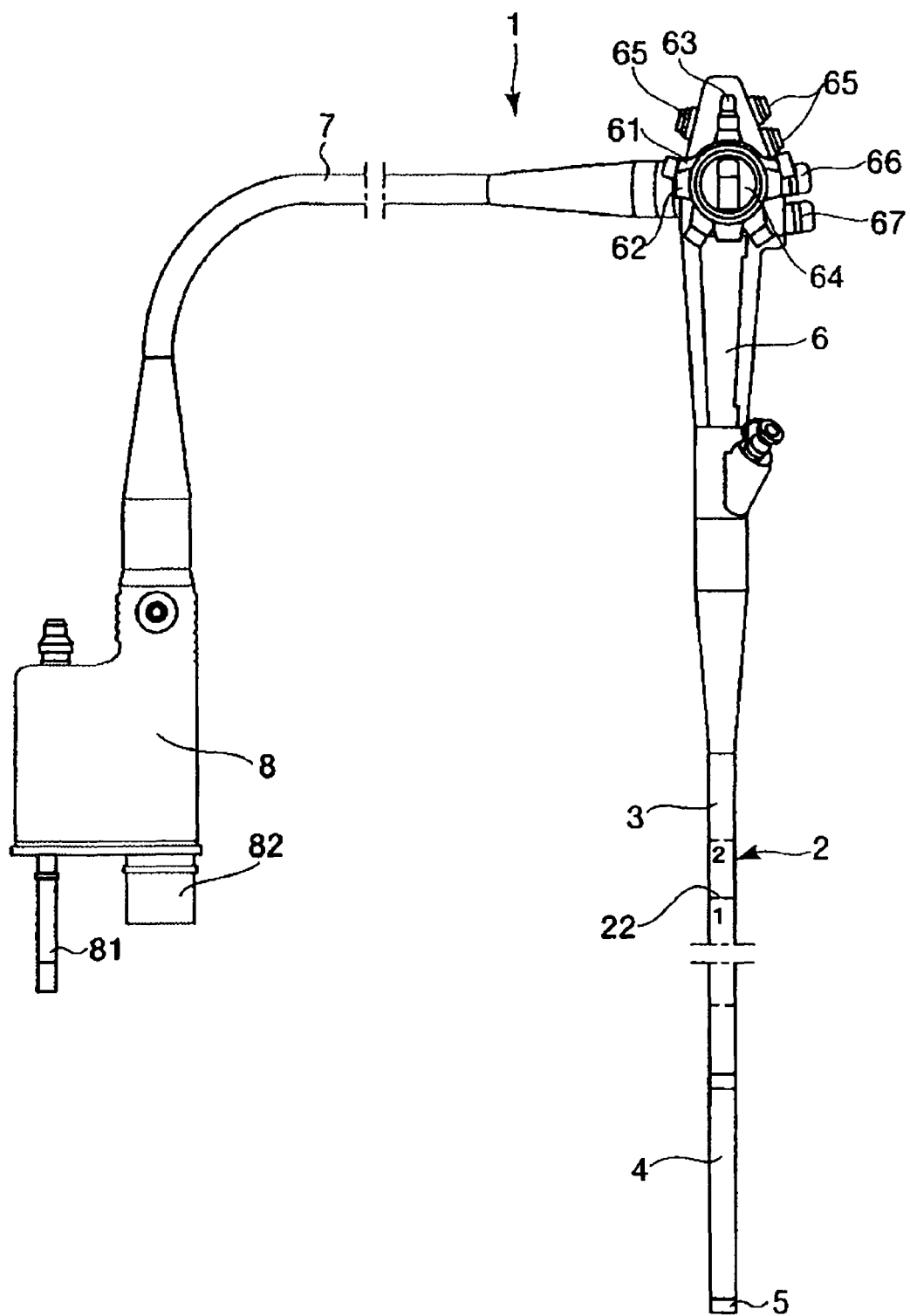
FIG. 1 is an overall view showing an embodiment wherein an endoscope according to the present invention is applied to an electronic endoscope (electronic scope).
Figure 2:
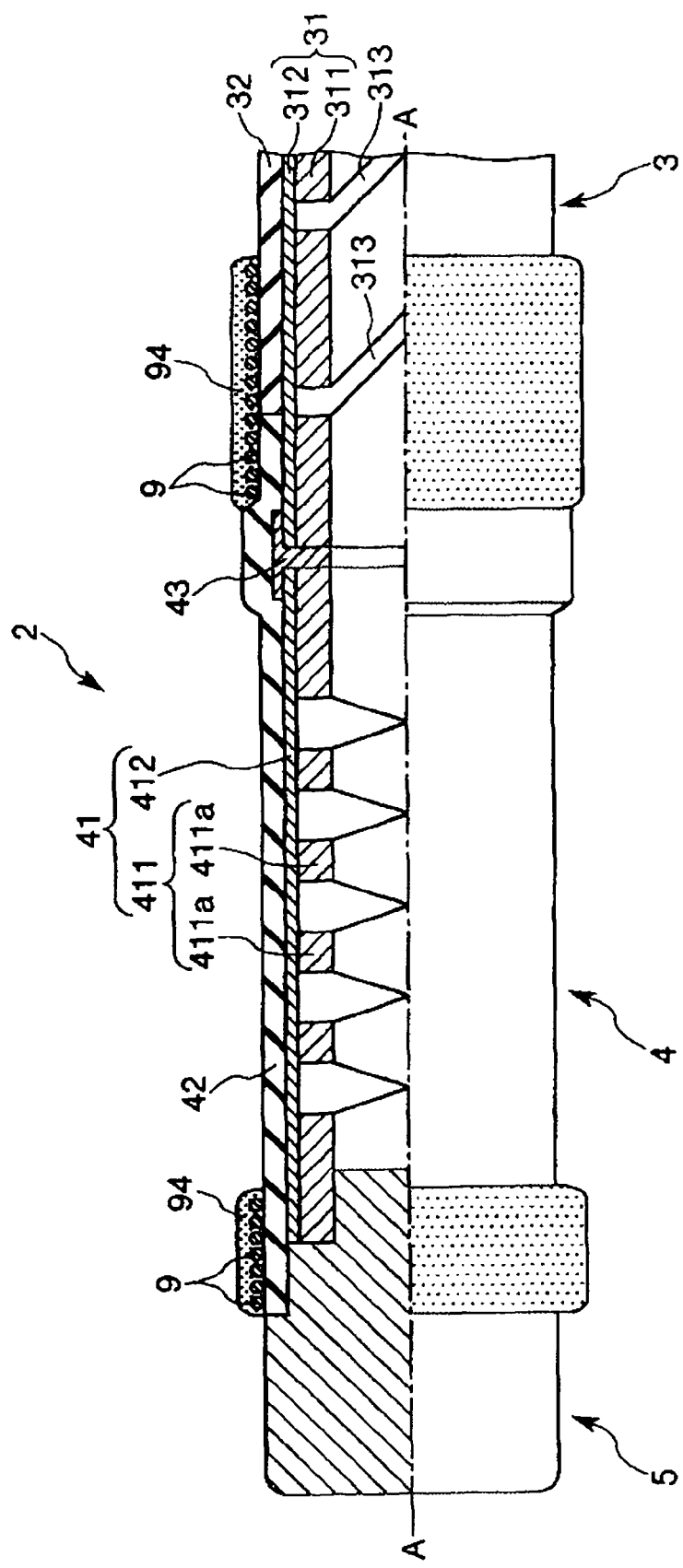
FIG. 2 is a partially cross-sectional view showing an insertion section flexible tube (flexible tube for an endoscope of the present invention) provided in the electronic endoscope of FIG. 1.

FIG. 1 is an overall view showing an embodiment wherein an endoscope according to the present invention is applied to an electronic endoscope (electronic scope), and FIG. 2 is a partially cross-sectional view showing an insertion section flexible tube (a flexible tube for an endoscope of the present invention) provided in the electronic endoscope of FIG. 1. In this connection, it should be appreciated that, in the following description, the upper side and the lower side in FIG. 1 will be referred to as "base end" and "tip end", respectively, and the right side and the left side in FIG. 2 will be referred to as "base end" and "tip end", respectively.

An electronic endoscope 1 shown in FIG. 1 includes an elongated insertion section flexible tube 2 having a prescribed flexibility (bendability), an operating section 6 connected to a base end of the flexible tube 2 so that it can be grasped by an operator to manipulate the entirety of the electronic endoscope 1, a connecting section flexible tube 7 connected to the operating section 6, and a light source plug 8 provided on a tip end of the connecting section flexible tube 7.

When in use, the flexible tube 2 is adapted for insertion into, e.g., a tubular cavity (body cavity) of a living body (patient). As shown in FIG. 1, the flexible tube 2 has a flexible tubular portion 3 and a bendable portion 4 provided on a tip end of the flexible tubular portion 3 for bending manipulation. These components are arranged in this order from a base end of the flexible tube 2.

Each of the flexible tubular portion 3 and the bendable portion 4 has an internal space in which various components such as an optical fiber, image signal cables, various tubes and the like (not shown in the drawings) are disposed and inserted.

As shown in FIG. 2, the flexible tubular portion 3 is provided with a core member 31 and an outer cover 32 which covers an outer periphery of the core member 31.

The core member 31 is comprised of a helical tube 311 and a lattice tube (braided member) 312 which is provided over an outer periphery of the helical tube 311, so that they provide an elongated tubular configuration as a whole.

The helical tube 311 is formed by winding a thin band-shaped member into a spiral shape of uniform diameter, with a spacing 313 left between adjoining turns of the band-shaped member. Preferably, stainless steel, copper alloy or the like may be used as a material for the band-shaped member.

The lattice tube 312 is formed by braiding a plurality of bundles of made of metallic or non-metallic fine wires. Preferably, stainless steel, copper alloy or the like, for example, may be used as a material for the fine wires. Furthermore, at least one of the fine wires forming the lattice tube 312 may be coated with a synthetic resin, although not shown in the drawings.

The entire parts of the core member 31 except for the tip end thereof are covered with the outer cover 32. The outer cover 32 is mainly formed of resin materials.

The resin materials should have flexibility or elasticity. Examples of the resin materials include, but are not particularly limited thereto, polyolefin such as polyethylene, polypropylene,. ethylene-propylene copolymer and ethylene-vinyl acetate copolymer (EVA); cyclic polyolefin; modified polyolefin; polyvinyl chloride; polyvinylidene chloride; polystyrene; polyamide; polyimide; polyamide imide; polycarbonate; poly-(4-methylpentene-1); ionomer; acryl-based resin; polymethyl methacrylate; acrylonitrile-butadiene-styrene copolymer (ABS resin); acrylonitrile-styrene copolymer (AS resin); butadiene-styrene copolymer; polyoxymethylene; polyvinyl alcohol (PVA); ethylene-vinyl alcohol copolymer (EVOH); polyester such as polyethylene terephthalate (PET), polybutylene terephthalate (PBT) and polycyclohexane terephthalate (PCT); polyether; polyether-ketone (PEK); polyether-ether-ketone (PEEK); polyether imide; polyacetal (POM); polyphenylene oxide; modified polyphenylene oxide; polysulphone; polyether sulphone; polyphenylene sulphide; polyarylate; aromatic polyester (liquid crystal polymer); polytetrafluoroethylene; polyvinylidene fluoride; other fluorine-based resins; various thermoplastic elastomers such as styrene-based elastomer, polyolefin-based elastomer, polyvinyl chloride-based elastomer, polyurethane-based elastomer, polyester-based elastomer, polyamide-based elastomer, polybutadiene-based elastomer, transpolyisoprene-based elastomer, fluoro-rubber-based elastomer and chlorinated polyethylene-based elastomer; and copolymers, blends or polymer alloys mainly composed of the above-listed materials. One of these materials may be used independently or two or more of these materials may be used in combination. If these kinds of flexible resin materials are used as a main constituent of the outer cover 32, it becomes possible for the tightening string for an endoscope (described later) to bite into the outer cover 32 in the process of tightening or winding the tightening string onto the outer cover 32, thus ensuring that the outer cover 32 is firmly secured to the core member 31.

The average thickness of each of the outer cover 32 and the outer cover 42 set forth below is preferably in the range of about 100 to 3,000 μm, and more preferably 200 to 1,000 μm, although there is no particular limitation in the average thickness as far as it is possible to protect the built-in components disposed inside the flexible tubular portion 3 and the bendable portion 4 and, further, the flexibility and the bendability of the flexible tubular portion 3 and the bendable portion 4 are not impaired.

Referring back to FIG. 1, the flexible tubular portion 3 is provided at its external surface with scales 22 for indicating the depth that the flexible tubular portion 3 is inserted into the body cavity. This allows an operator to manipulate the flexible tube 2 while looking the scales 22, when the flexible tube 2 is inserted into the body cavity. It is therefore possible to surely guide the tip end of the flexible tube 2 to a desired position.

The bendable portion 4 is coupled to the tip end of the flexible tubular portion 3.

As shown in FIG. 2, the bendable portion 4 includes a core member 41 and an outer cover 42 covering an outer periphery of the core member 41.

The core member 41 is comprised of a nodal ring assembly 411 and a lattice tube 412 enclosing an outer periphery of the nodal ring assembly 411 so that they form an elongated tubular configuration as a whole.

The nodal ring assembly 411 is comprised of a plurality of nodal rings 411a with a cross-section of generally annular shape. These nodal rings 411a are disposed side by side along a center axis A of the nodal ring assembly 411. In this nodal ring assembly, the mutually adjacent nodal rings 411a are joined to each other by means of a rivet (not shown in the drawings) and can make an inclined movement with respect to one another. Stainless steel, copper alloy or the like may be preferably used as a material for the nodal rings 411a.

Further, wire guides (not shown) are provided on predetermined nodal rings 411a which are positioned on every predetermined numbers of nodal rings 411a. A rigid portion 5 described below is connected to the wire guides, and bendable portion operating wires, each of which continually extends within the bendable portion 4 and the flexible tubular portion 3, are inserted through the wire guides. The bendable portion operating wires are provided, for example, in two sets each including a pair of wire strands. By pulling or releasing each of the bendable portion operating wires, the bendable portion 4 is bent in an arbitrary direction in accordance with the inclined movement of the nodal rings 411a.

At this time, the bendable portion operating wires are supported by the wire guides in such a manner that they can move toward or away from the tip end and the base end.

The outer periphery of the nodal ring assembly 411 is covered with a lattice tube 412 that has the same configuration as the lattice tube 312 described above.

The base end of the core member 41 is connected through a connecting tube 43 to the tip end of the core member 31 of the flexible tubular portion 3.

The outer periphery of the core member 41 is covered with the outer cover 42 beyond the opposite ends of the core member 41. The opposite ends of the outer cover 42 are adapted to respectively enclose the base end of the rigid portion 5 (described below in detail) and the tip end of the core member 31 of the flexible tubular portion 3. In other words, the base end of the rigid portion 5 and the tip end of the core member 31 are respectively inserted (disposed) inside the opposite ends of the outer cover 42.

By the outer cover securing method according to the present invention, the tip end of the outer cover 42 of the bendable portion 4 is secured to the rigid portion 5 (a member provided inside the outer cover), and the base end of the outer cover 42 of the bendable portion 4 and the tip end of the outer cover 32 of the flexible tubular portion 3 are respectively secured to the core member 31 (a member provided inside the outer cover) of the flexible tubular portion 3.

The outer cover 42 is mainly formed of a material. Since the rubber material has elasticity, it becomes possible for the below-mentioned tightening string for an endoscope to bite into the outer cover 42 in the process of tightening the outer cover 42 with the tightening string for an endoscope, thus ensuring that the outer cover 42 is firmly secured to the core member 31.

Examples of the rubber materials include, but are not particularly limited to: butadiene-based rubber such as natural rubber (NR), isoprene rubber (IR), butadiene rubber (BR, 1,2-BR) and styrene butadiene rubber (SBR); diene-based special rubber such as chloroprene rubber (CR) and butadiene-acrylonitrile rubber (NBR); olefin-based rubber such as butyl rubber (IIR), ethylene-propylene rubber (EPM, EPDM), acrylic rubber (ACM, ANM) and halogenated butyl rubber (X-IIR); urethane-based rubber such as urethane rubber (AU, EU); ether-based rubber such as hydrin rubber (CO, ECO, GCO, EGCO); polysulfide-based rubber such as polysulfide rubber (T); silicone rubber (Q); fluoro rubber (FKM, FZ); and chlorinated polyethylene (CM). One of these materials may be used independently or two or more of these materials may be used in combination.

Further, the rigid portion 5 is attached to the tip end of the bendable portion 4. The rigid portion 5 is constructed from a block of cylindrical shape.

Provided inside the rigid portion 5 is an image-taking element (CCD) not shown in the drawings that takes images of an object on the observation area. The image-taking element is connected to an image signal connector 82 provided on the light source plug section 8, by means of an image signal cable (not shown) continuously extending through the insertion section flexible tube 2, the operating section 6 and the connecting section flexible tube 7.

Moreover, the rigid portion 5 is joined to the tip end of the bendable portion operating wires.

Examples of the constituent materials for the rigid portion 5 include, but are not particularly limited to, stainless steel, aluminum, aluminum alloy, titanium and titanium alloy.

A light source connector 81 is provided on the tip end of the light source plug section 8 in parallel with the image signal connector 82. By plugging the light source connector 81 and the image signal connector 82 in a connecting section of a light source processor device (not shown), the light source plug section 8 is connected to the light source processor device. A monitor device (not shown) is connected to the light source processor device via a cable.

The light emitted from the light source processor device is transmitted to the rigid portion 5 through the light source connector 81 and a light guide (not shown) continuously disposed within the light source plug section 8, the connecting section flexible tube 7, the operating section 6 and the insertion section flexible tube 2. Then, the light is irradiated from the tip end of the rigid portion 5 on a target observation area to illuminate the area. The light guide is comprised of a plurality of tied-up light guide members that may be made of, e.g., quartz, multi-component glass, plastic and the like.

The light (object images) reflected from the observation area thus illuminated is sensed by the image-taking element which in turn generates image signals corresponding to the images taken The image signals are transmitted to the light source plug section 8 through the image signal cable.

And, the image signals is subject to prescribed processing (e.g., signal processing and an image processing) in the light source plug section 8 and the light source processor device, after which the image signals are inputted to the monitor device. The monitor device is adapted to display the images (electronic images) taken by the image-taking element, namely, the motion images monitored by the endoscope.

Further, a first operating knob 61, a second operating knob 62, a first lock lever 63 and a second lock lever 64 are provided on the top surface (in FIG. 1) of the operating section 6 in an independently rotatable manner.

In response to the rotating operation of the operating knobs 61 and 62, the bendable portion operating wires (not shown) disposed within the insertion section flexible tube 2 are pulled to thereby make the bendable portion 4 bend in four directions, which makes it possible to change the bending direction of the bendable portion 4.

Further, if each of the lock levers 63 and 64 is rotated counterclockwise, it becomes possible to lock (keep) the bendable portion 4 in a bent condition (in up-and-down and right-and-left directions). On the other hand, if each of the lock levers 63 and 64 is rotated clockwise, it becomes possible to release the bendable portion 4 from the locked condition.

A plurality of (three, in the present embodiment) control buttons 65, a suction button 66 and a gas supply/liquid supply button 67 are provided on the side surface or peripheral surface (in FIG. 1) of the operating section 6.

By pushing the control buttons 65 under a state that the electronic endoscope 1 is coupled to the light source processor device (external device), it is possible to remote control various operations of the light source processor device, the monitor device and the like (for example, changing-over of electronic images from motion images to still images and vice versa, starting and/or stopping of an electronic image filing system or an image-taking device, and starting and/or stopping of an electronic image recording device).

The suction button 66 and the gas supply/liquid supply button 67 serve to open and close a suction channel and a gas supply/liquid supply channel (any of them not shown in the drawings), each of which continuously extends through the light source plug section 8, the connecting section flexible tube 7, the operating section 6 and the insertion section flexible tube 2, with one end thereof opened at the tip end of the flexible tube 2 and the other end thereof opened at the light source plug section 8.

Namely, unless the suction button 66 and the gas supply/liquid supply button 67 are pushed, the suction channel and the gas supply/liquid supply channel remain closed (in a condition permitting no fluid to pass therethrough). On the other hand, if an operator pushes the suction button 66 and the gas supply/liquid supply button 67, the suction channel and the gas supply/liquid supply channel are opened (in a condition permitting fluid flow therethrough).

Further, when the electronic endoscope 1 is in use, a suction means is coupled to the other end of the suction channel and a gas supply/liquid supply means is connected to the other end of the gas supply/liquid supply channel.

Thus, when the suction channel is in the opened condition, body fluid, blood or the like within the body cavity can be sucked up from the tip end of the flexible tube 2. Further, when the gas supply/liquid supply channel is in the opened condition, it is possible to supply liquid or gases into the body cavity from the tip end of the insertion section flexible tube 2.

Now, description will be given as to an outer cover securing method according to the present invention.

Hereinbelow, the outer cover securing method according to the present invention will be described, based on an exemplary case where a flexible tubular portion and a bendable portion are bonded (coupled) in an insertion section flexible tube of the endoscope shown in FIG. 1.

Figure 3:
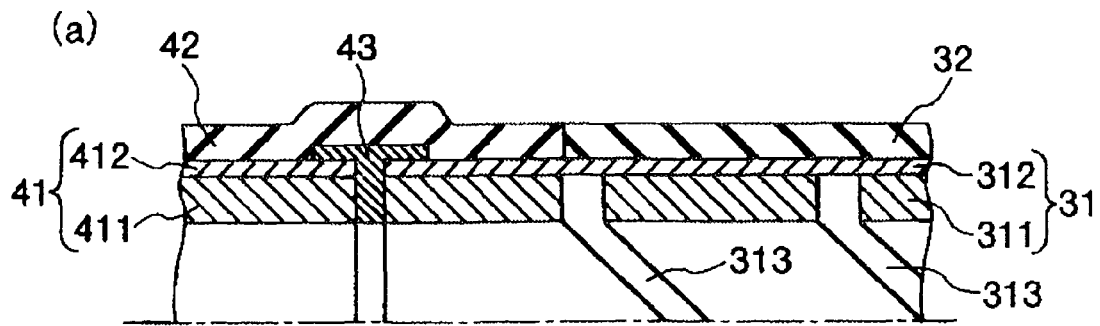
FIG. 3 is a partially cross-sectional view illustrating an outer cover securing method in accordance with the present invention.
Figure 3:
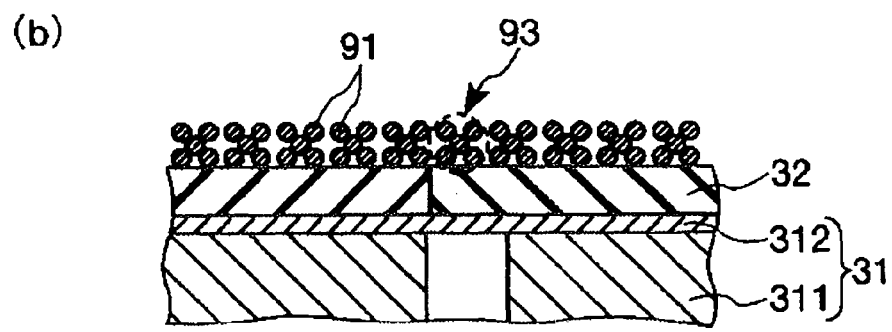
Figure 3:
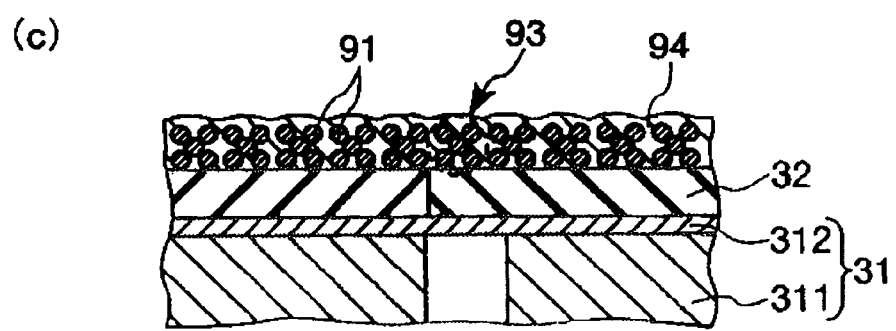

FIG. 3 is a view (partially cross-sectional view) illustrating an outer cover securing method in accordance with the present invention, wherein (b) and (c) show an outer cover and its neighboring structure in an enlarged condition. Hereinbelow, it should be noted that the term "outer cover" is used to denote each of an outer cover 32 and an outer cover 42 or both the outer cover 32 and the outer cover 42 on occasions

[1] Prepared first are a flexible tubular portion 3 that has a core member 31 and an outer cover 32 covering the outer periphery of the core member 31 and a bendable portion 4 that has a core member 41 and an outer cover 42 covering the outer periphery of the core member 41.

Then, as shown in FIG. 3(a), the tip end of the core member 31 is connected (coupled) to the base end of the core member 41 through the use of a connecting tube 43, and the tip end of the core member 31 is covered with the outer cover 42 (First Step).

Subsequently, as shown in FIG. 3(b), the tip end of the outer cover 32 and the base end of the outer cover 42 are tightened continuously from the external surface thereof by means of a tightening string 9 for an endoscope (Second Step).

According to the present invention, the tightening string 9 is comprised of a filament assembly 93 formed by bundling a plurality of filaments (monofilaments) 91 made of a synthetic resin.

As used herein, the term "filament made of a synthetic resin" means a single strand of long fiber formed continuously without any joining part, which differs from a natural fiber comprised of staples (short fibers).

Construction of the tightening string 9 will be described in detail later.

Then, as illustrated in FIG. 3(c), the tightening string 9 is covered with an adhesive agent 94 and bonded together in place (Third Step).

Thus, the tightening string 9 is affixed to the external surface of the outer cover 32 and the outer cover 42 by the adhesive agent 94 under the state that it tightens the outer cover 32 and the outer cover 42. Further, by covering and bonding the tightening string 9 with the adhesive agent 94, the tightening string 9 is prevented from any unwanted loosening or separation. In addition, the boundary region between the outer cover 32 and the outer cover 42 is also covered with the adhesive agent 94, which assures high liquid-tightness in between the flexible tubular portion 3 and the bendable portion 4.

Figure 7:
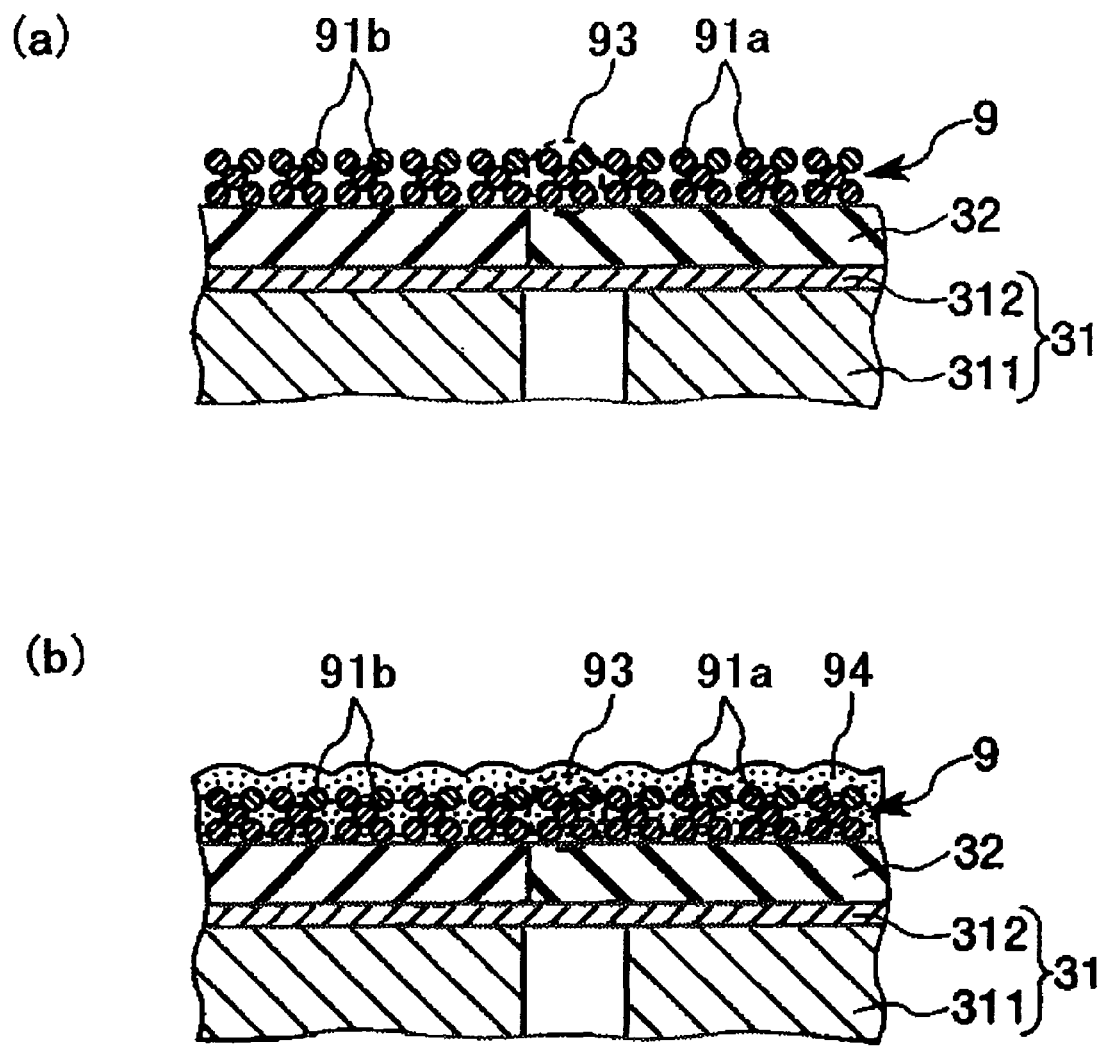
FIG. 7 is a partially cross-sectional view illustrating an outer cover securing method in accordance with the present invention, wherein FIG. 7(a) and FIG. 7(b) respectively show the second step and the third step of the method for fourth to seventh embodiments of the present invention.

In this connection, please note that in the fourth to seventh embodiments which will be described later, the tightening string 9 is constituted from a filament assembly 93 obtained by twisting filament twists formed from first filaments 91a and second filaments 91b. Therefore, in the fourth to seventh embodiments, the second step described above corresponds to the step shown in FIG. 7(a) and the third step described above corresponds to the step shown in FIG. 7(b).

It is preferred that the adhesive agent 94 is mainly comprised of at least one of an epoxy-based adhesive agent, a urethane-based adhesive agent, an acryl-based adhesive agent and an ester-based adhesive agent. These adhesive agents are relatively high in a chemical resistance and a heat resistance. Therefore, the adhesive agent 94 is prevented from degeneration or degradation even in the case that the electronic endoscope 1 is repeatedly subject to a disinfecting or sterilizing treatment. Owing to this, the tightening string 9 can reliably keep the outer cover 32 and the outer cover 42 secured onto the core member 31 and the core member 41. Further, it is also possible to maintain enhanced liquid-tightness between the flexible tubular portion 3 and the bendable portion 4 for a prolonged period of time.

Although there exists no restriction in a curing method, the adhesive agent 94 may have a curing property as can be seen in a hot-melt type, thermally curable type or photo-curable type adhesive agent. Further, the adhesive agent 94 may be supplied to the external surface of the outer cover 32 and the outer cover 42 in a single kind of adhesive agent liquid or two kinds of adhesive agent liquids mixed with each other.

In the meantime, the electronic endoscope 1 is repeatedly disinfected or sterilized with chemicals. By covering the tightening string 9 with the adhesive agent 94, it is possible to prevent the tightening string 9 from contacting with water, chemicals or the like. Accordingly, the synthetic resin from which the filament 91 is made can be selected from various kinds of resins merely from a view point of functions and costs but without having to consider the relative merits in terms of a water resistance, a chemical resistance or the like.

Moreover, by covering the tightening string 9 with the adhesive agent 94, the ridges-and-valleys formed on the external surface of the insertion section flexible tube 2 along the contour of the tightening string 9 are lessened or eliminated by the adhesive agent 94. Thus, it is possible to prevent a patient from suffering increased pain in the process of inserting the flexible tube 2 into the body cavity. Further, such lessening or eliminating of the ridges-and-valleys makes it possible to reliably remove contaminants on its surface during the course of cleansing.

Now, description will be given regarding the construction of the tightening string 9 for an endoscope.

As set forth above, the tightening string 9 for an endoscope according to the present invention is comprised of a filament assembly 93 formed by bundling a plurality of filaments 91 made of a synthetic resin. Unlike a natural fiber formed of staples (short fibers), the synthetic resin-made filament 91 is a pliant and quite long fiber. Thus, it is possible to prevent the tightening string 9 (filaments 91) from any severing, when wound around and tightened onto the outer cover 32 and the outer cover 42. As a result, when the tightening string 9 has been covered with an adhesive agent 94, it is possible to avoid any protrusion of the ends of the filaments 91 to the outside from the adhesive agent 94 or any creation of a micro-asperity (fluff or fuzz) on the surface of the adhesive agent 94. Therefore, it is possible for the tightening string 9 to reliably secure the outer cover 32 and the outer cover 42 onto the core member 31.

Furthermore, since the filament assembly 93 is formed by bundling the plurality of filaments 91 together, gaps exist between the filaments 91. Therefore, an anchor effect is created when the adhesive agent 94 is infiltrated into the gaps between the filaments 91 and the gaps between the adjacent strands of the filament assembly 93. This anchor effect makes it possible for the adhesive agent 94 to secure the tightening string 9 with greater adhesive strength.

<First Embodiment>

Initially, description will be made with regard to a first embodiment of a tightening string for an endoscope according to the present invention.

Figure 4:
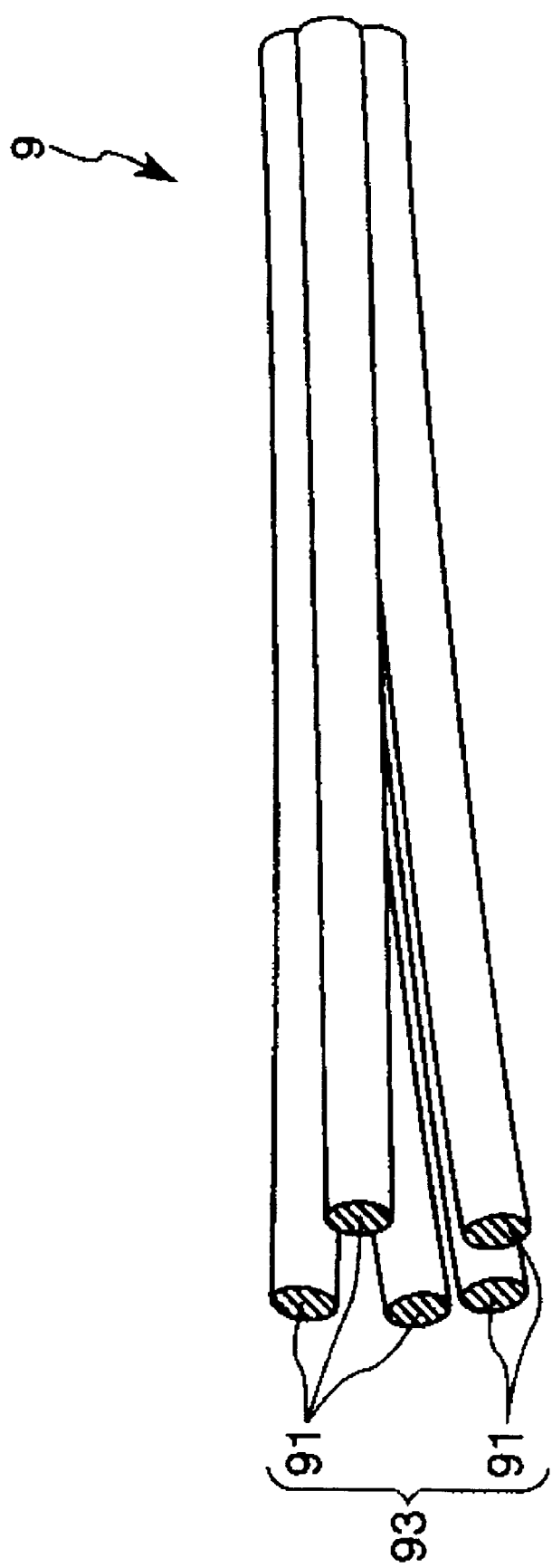
FIG. 4 is a perspective view showing a first embodiment of a tightening string for an endoscope in accordance with the present invention.

FIG. 4 is a perspective view showing a first embodiment of a tightening string for an endoscope in accordance with the present invention.

The tightening string 9 shown in FIG. 4 is comprised of a filament assembly 93 obtained by bundling a plurality of filaments 91 in a rectilinearly arranged condition.

In this tightening string 9, a relationship B/A is preferably in the range of about 2 to 30, more preferably in the range of about 3 to 25, and most preferably in the range of about 5 to 20, where A denotes the outer diameter (mm) of each of the filaments 91 and B represents the outer diameter (mm) of the filament assembly 93. If the outer diameters of the filaments 91 and the filament assembly 93 satisfy the above relationship, an appropriate size of ridges-and-valleys are formed on the region tightened by the tightening string 9. At the time of securing the tightening string 9 with an adhesive agent 94, the adhesive agent 94 is spread into the ridges-and-valleys by the capillary phenomenon. Thus, by a stronger anchor effect, the adhesive agent 94 is bonded to the tightening string 9 with greater adhesive strength. As a result, it is possible for the adhesive agent 94 to reliably secure the tightening string 9 in place.

More specifically, the outer diameter of each of the filaments 91 is preferably in the range of about 0.001 to 0.035 mm (1 to 35 dtex), and more preferably about 0.003 to 0.016 mm (3 to 16 dtex). By using the filament 91 having a relatively small size, the filaments 91 can be bundled in plural number to form the tightening string 9. This makes it possible to increase the surface area of the tightening string 9, thus making greater the anchor effect of the adhesive agent 94.

As used herein, "dtex" means a unit representing the fineness of a yarn. 1 dtex represents the outer diameter of a yarn whose length is 10,000 m and whose mass is 1 g, whereas 1 tex represents the outer diameter of a yarn whose length is 1,000 m and whose mass is 1 g. This means that the greater the fineness of a yarn, the smaller the outer diameter thereof.

Further, the outer diameter of the filament assembly 93 varies with the outer diameter of the filaments 91 and is preferably within a range of, but should not be particularly limited to, about 0.05 to 0.15 mm (50 to 150 dtex), and more preferably about 0.075 to 0.125 mm (75 to 125 dtex). By employing the filament assembly 93 whose outer diameter falls within the above range, it becomes possible for the filament assembly 93 to form the tightening string 9 with sufficient strength without having to unnecessarily increase the outer diameter of the insertion section flexible tube 2.

As set forth above, each of the filaments 91 is made of a synthetic resin. It is preferred that the synthetic resin has polar structures in its main chains and/or side chains. This strengthens the interaction between the polar structures and the adhesive agent 94 and thus can enhance the bonding strength between the filaments 91 and the adhesive agent 94.

The synthetic resin may include, as the polar structures, at least one of —OH, —CHO, —NCO, —COOH, —NO$_2$, —NH$_2$, —SH, —SO$_3$H, —CN, —O—, —CO—, —COO—, —CONH—, —CONHCO—, —NHCOO— and —S—. It is preferred that the synthetic resin include, as the polar structures, at least one of —OH, —CHO, —NCO, —COOH, —O—, —CO—, —COO—, —CONH—, —CONHCO— and —NHCOO—. These polar structures are contained in great quantity within a constituent material of the adhesive agent 94. Therefore, by permitting the main chains and/or side chains to contain the polar structures, it becomes possible to make greater the bonding strength between the filaments 91 and the adhesive agent 94.

Specific examples of the synthetic resin include: polyamide-based resin such as nylon 6, nylon 66, nylon 612 and aramid; polyvinyl alcohol-based resin; polyurethane-based resin; polyester-based resin such as polyethylene terephthalate and polybutylene terephthalate; and acryl-based resin such as polymethylmethacrylate, polyethylmethacrylate, methacrylic ester and acrylic acid ester. One of these resins may be used independently or two or more of these resins may be used in combination.

In the present embodiment, although the filament assembly 93 may be obtained by merely bundling a plurality of filaments 91, it is preferred that the filaments 91 are bonded (fixed) to one another at least partially along a longitudinal direction thereof. This increases the tying force with which the filaments 91 are bundled together. It is therefore possible for the tightening string 9 to keep the outer cover 32 and the outer cover 42 in the secured condition for an extended period of time and in a stabilized manner.

Examples of the method for fixing the filaments 91 to one another include an adhesively bonding method and fusion bonding method (e.g., thermal fusion bonding, ultrasonic fusion bonding and high-frequency fusion bonding).

Furthermore, the synthetic resin preferably has a melting point or softening point of 150° C. or higher, and more preferably 170° C. or higher. This imparts sufficient durability to the tightening string 9 against a disinfecting or sterilizing treatment conducted in an autoclave or the like under an elevated temperature. As a result, even though the electronic endoscope 1 is repeatedly subject to a sterilizing treatment (particularly, an autoclave sterilization), it is possible to keep high the liquid-tightness between the flexible tubular portion 3 and the bendable portion 4 reliably for a prolonged period of time.

Moreover, it is desirable that the filaments 91 be easily elongated as far as possible. Specifically, it is preferred that each of the filaments 91 has an elongation ratio (breaking elongation ratio) of greater than 10%, and more preferably greater than 15%, wherein the elongation ratio means a value measured by applying a tensile force to each of the filaments 91 to a breaking point. By imparting such a great elongation ratio to the filaments 91, it becomes possible to prevent the filaments 91 from severing even in the case that the tightening string 9 is given a shock accompanying, e.g., a suddenly acting heavy tensile force, or a thermal shock.

<Second Embodiment>

In the next place, description will be given with regard to a second embodiment of a tightening string for an endoscope according to the present invention.

Figure 5:
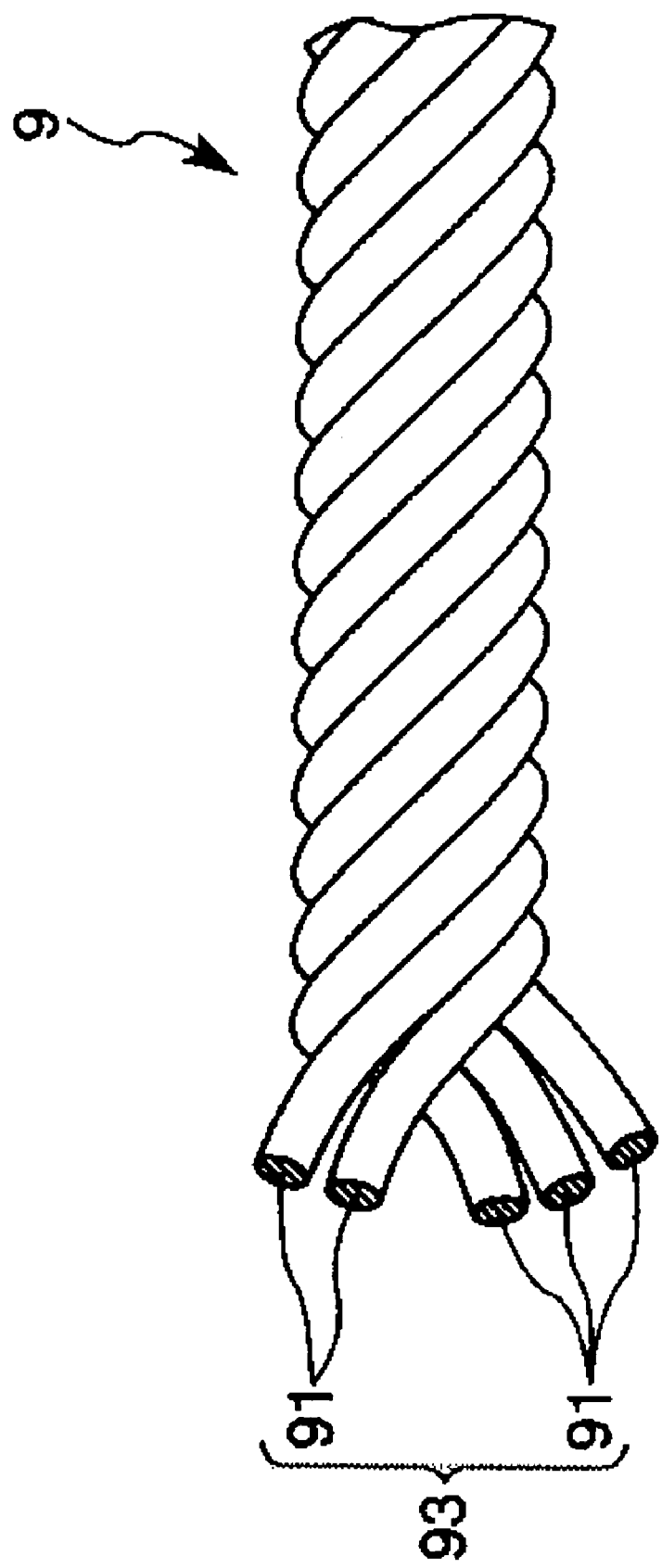
FIG. 5 is a perspective view showing a second embodiment of a tightening string for an endoscope in accordance with the present invention.

FIG. 5 is a perspective view showing the second embodiment of a tightening string for an endoscope in accordance with the present invention.

The following description for a second embodiment will be focused on the points differing from the first embodiment and no description will be offered regarding the same matters as in the first embodiment.

The tightening string 9 for an endoscope shown in FIG. 5 is comprised of a filament assembly 93 obtained by twisting a plurality of filaments 91.

This filament assembly 93 is produced by bundling the plurality of filaments 91 together and twisting the same. At this time, the number of twisting may preferably be, but is not particularly limited to, about 1,000 to 5,000 T/m, and more preferably about 2,000 to 5,000 T/m. As used herein, "T/m" means the number of twisting (twist count) per meter.

In this connection, it should be appreciated that there is no particular restriction in the direction of twist of the filament assembly 93.

Further, although the filament assembly 93 may be obtained by merely twisting the plurality of filaments 91, it is preferred that the filaments 91 are bonded (fixed) to one another at least partially along a longitudinal direction thereof. This makes it possible to prevent the filaments 91 from any untwisting (restoring to the original shape) which may otherwise take place by the resilient force of the filaments 91. It is therefore possible to keep the filament assembly 93 in the twisted condition for an extended period of time and in a stabilized manner.

The filaments 91 thus twisted can be fixedly secured to one another in the following manner, for example.

At first, the plurality of filaments 91 is bundled together and twisted into the filament assembly 93.

Then, the filament assembly 93 is heated either in a wet atmosphere or in a dry atmosphere. This induces rearrangement of the inter-molecular bonds in the filaments 91, thus allowing the shape of the filaments 91 to be stably kept in the twisted condition. Accordingly, the filaments 91 are entwined with one another and can be at least partially fixed along a longitudinal direction thereof.

In this process, the heating temperature is preferably in the range of about 100 to 200° C.

Further, during the heating process, the filaments 91 can be stably fixed in a more reliable manner by applying a pressing force and/or a tensile force to the filament assembly 93.

According to the tightening string 9 of the second embodiment as described above, it is possible to obtain the same operations and effects as in the first embodiment.

Namely, by twisting the filaments 91 in this manner, alternating ridges-and-valleys are periodically formed on the surface of the filament assembly 93. The adhesive agent 94 is spread into the ridges-and-valleys to thereby provide a stronger anchor effect with respect to the tightening string 9 so that the tightening string 9 can be bonded with greater adhesive strength. As a result, it is possible for the adhesive agent 94 to reliably secure the tightening string 9 in place.

<Third Embodiment>

In the next place, description will be given with regard to a third embodiment of a tightening string for an endoscope according to the present invention.

Figure 6:
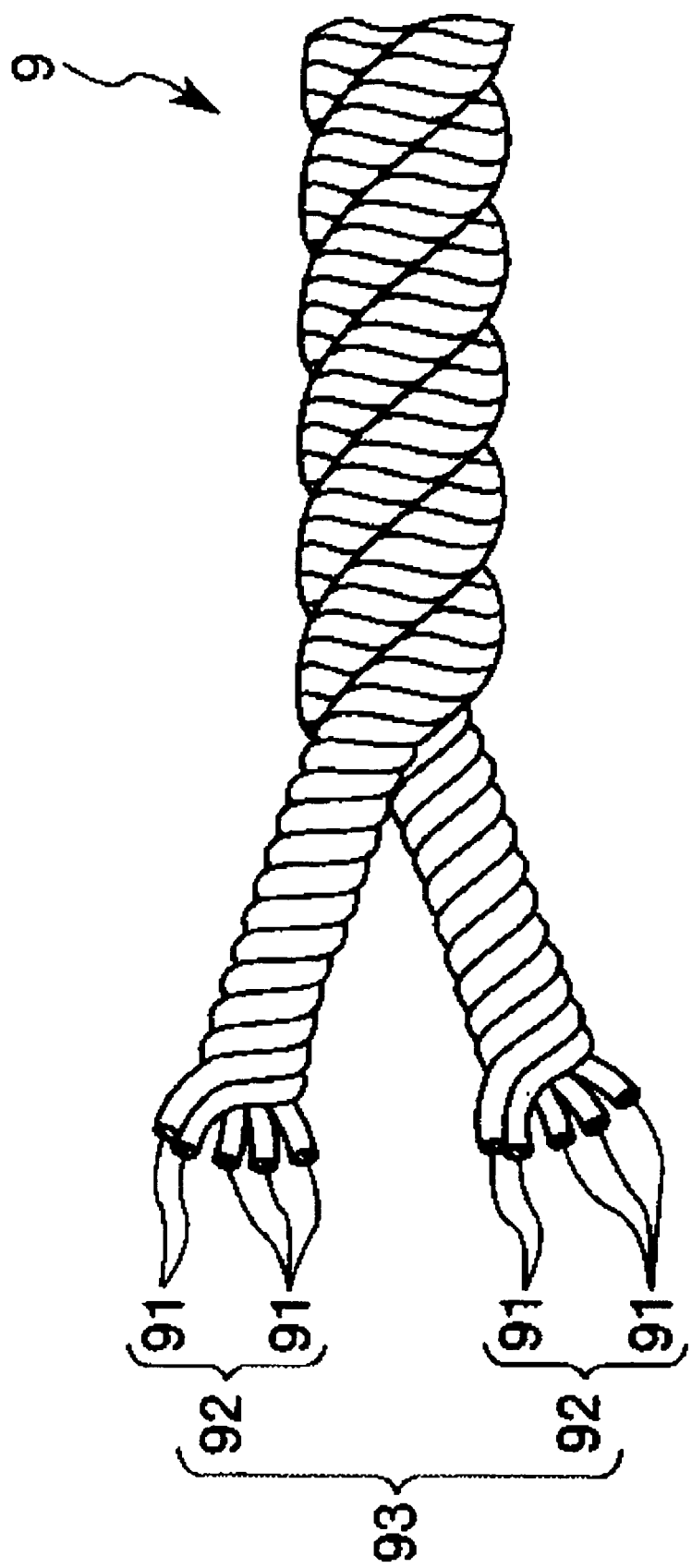
FIG. 6 is a perspective view showing a third embodiment of a tightening string for an endoscope in accordance with the present invention.

FIG. 6 is a perspective view showing the third embodiment of a tightening string for an endoscope in accordance with the present invention.

The following description for a third embodiment will be focused on the points differing from the first and second embodiments, and no description will be offered regarding the same matters as in the first and second embodiments.

The tightening string 9 for an endoscope shown in FIG. 6 makes use of a filament twist (multi-filament) 92 formed by twisting a plurality of filaments 91, and is comprised of a filament assembly 93 obtained by further twisting a plurality of the filament twists 92.

The outer diameter of each of the filament twists 92 is preferably in the range of about 0.01 to 0.075 mm (10 to 75 dtex), and more preferably about 0.025 to 0.070 mm (25 to 70 dtex).

This type of filament assembly 93 is produced by bundling the plurality of filament twists 92 together and then twisting the same. At this time, the number of twisting (upper or secondary twisting) of the filament twists 92 is properly selected depending on the number of twisting (lower or primary twisting) of the filaments 91 in the filament twists 92 and may preferably be within a range of, but is not limited to, about 600-3,000 T/m, and more preferably about 1,200-3,000 T/m.

Moreover, in this twisting process, no particular limitation is imposed on the twisting direction of the filament assembly 93. Also, the twisting direction of the filament twists 92 relative to the twisting direction of the filament assembly 93 is subject to no particular limitation but may preferably be different from each other. This helps to keep each of the filament twists 92 and the filament assembly 93 from untwisting.

Further, although the filament assembly 93 may be formed by merely twisting the plurality of filament twists 92, it is preferred that the filament twists 92 are bonded to one another at least partially along a longitudinal direction thereof. This makes it possible to prevent the filament twists 92 from any untwisting which may otherwise take place by the resilient force of the filament twists 92. It is therefore possible to keep the filament assembly 93 in the twisted condition for an extended period of time and in a stabilized manner.

The task of fixing the filament twists 92 to one another may be carried out in the same manner as the filaments 91 are bonded to one another in the second embodiment described above.

According to the tightening string 9 of the third embodiment as described above, it is possible to obtain the same functions and effects as those in the first and second embodiments.

Namely, by further twisting the plurality of filament twists 92 to form filament assembly 93, a plurality of ridges-and-valleys are created on the surface of the filament assembly 93, thus greatly increasing the surface area of the filament assembly 93. This enables an anchor effect to be exhibited particularly strongly, thereby making it possible for the adhesive agent 94 to quite reliably secure the tightening string 9 in place. It is also possible to improve the mechanical strength of the tightening string 9 as a whole.

Further, in the tightening string 9 according to the present invention, it is possible to arbitrarily use two or more of the first through third embodiments in combination.

For example, the tightening string 9 may be comprised of a filament assembly 93 formed by combining one filament twist 92 and a plurality of filaments 91.

Furthermore, in the tightening string 9 according to the present invention, it is not necessary that the filament assembly 93 is formed of a synthetic resin, and other materials may be used for the filament assembly.

PRACTICAL EXAMPLES

Hereinbelow, practical examples of the present invention employing the tightening strings of the first to third embodiments described above will be described in more detail.

1. Production of Electronic Endoscope

In accordance with the following manner, fifteen electronic endoscopes shown in FIG. 1 were manufactured for each of Examples 1 to 4 and Comparative Examples 1 to 3.

Example 1

Initially, for each of the electronic endoscopes, a rigid portion, a bendable portion and a flexible tubular portion for the endoscope shown in FIG. 1 were prepared (using components of Endoscope FB-29X manufactured by Pentax Corporation, Japan).

Then, the base end of the rigid portion was inserted into and affixed to the tip end of an outer cover of the bendable portion, and the tip end of a core member of the flexible tubular portion was inserted into and affixed to the base end of an outer, cover of the bendable portion.

Subsequently, a tightening string for an endoscope was prepared.

This tightening string was constituted from a filament assembly obtained by twisting four first filaments and one second filament. The details of the constitution of the tightening string were as follow. In this regard, the elongation ratio of a filament was a value measured by Autograph (a product of Shimazu Corporation, Japan).

Constitution of Tightening String
Filament (Mono-filament)
  Constituent Material: nylon 6
  Softening Point: 210° C.
  Elongation ratio (at room temperature): 10% or more
  Outer Diameter (Fineness): 0.008 mm (8 dtex)
Filament Twist (Multi-filament)
  Number of Filament: 5
  Number of Twisting (Lower): 1,000 T/m
  Outer Diameter (Fineness): 0.04 mm (40 dtex)
Filament Assembly (Tightening String)
  Number of Filament Twist: 2
  Number of Twisting (Upper): 600 T/m
  Outer Diameter (Fineness): 0.08 mm (80 dtex)

Then, the tip end of the outer cover of the bendable portion, the base end of the outer cover of the bendable portion, and the tip end of the outer cover of the flexible tubular portion were tightened by the tightening string thus produced. Then, an adhesive agent mainly composed of an epoxy-based resin was supplied in such a manner as to cover the tightening string. Thereafter, the adhesive agent was heated at a temperature of 85° C. for one hour to cure the same, thus securing the tightening string in place.

Subsequently, an electronic endoscope was manufactured using the thus obtained bonded body (that is, an insertion section flexible tube of an endoscope). The details of the constitution of the respective portions were as follows.
Rigid Portion
  Constituent Material: aluminum alloy
  Shape: cylindrical, with three varying outer diameters
  Outer Diameter of Intermediate Part: 9 mm
Bendable Portion
  Dimension of Nodal Ring Assembly: outer diameter of 9 mm and inner diameter of 7 mm
  Constituent Material of Nodal Ring: stainless steel
  Constituent Material of Lattice tube: stainless steel
  Average Thickness of Outer Cover: outer diameter of 10 mm and inner diameter of 9 mm (average thickness of 500 μm)
  Constituent Material of Outer Cover: fluoro-rubber
Flexible Tubular Portion
  Dimension of Core Member: outer diameter of 9 mm and inner diameter of 7 mm
  Constituent Material of Helical tube: stainless steel
  Constituent Material of Lattice tube: stainless steel
  Dimension of Outer Cover: outer diameter of 10 mm and inner diameter of 9 mm (average thickness of 500 μm)
  Constituent Material of Outer Cover: polyurethane-based thermoplastic elastomer Example 2

An electronic endoscope was produced in the same manner as in Example 1, except that the constituent material of the filament was changed to vinyl on (polyvinyl alcohol-based resin).

Further, vinylon used had a softening point of 220° C. and the filament had an elongation ratio of 10% or higher.

Example 3

An electronic endoscope was produced in the same manner as in Example 1, except that the constituent material of the filament was changed to polyester.

Further, polyester used had a softening point of 240° C. and the filament had an elongation ratio of 10% or higher.

Example 4

An electronic endoscope was produced in the same manner as in Example 1, except that the constituent material of the filament was changed to polyurethane.

Further, polyurethane used had a softening point of 200° C. and the filament had an elongation ratio of 10% or higher.

Comparative Example 1

An electronic endoscope was produced in the same manner as in Example 1, except that a single strand of filament was used as the tightening string for an endoscope. The details of the constitution of the tightening string were as follows.
Constitution of Tightening String
Filament (Monofilament)
  Constituent Material: nylon 6
  Softening Point: 210° C.
  Elongation ratio: 10% or higher
  Number of Strand: 1
  Outer Diameter (Fineness): 0.08 mm (80 dtex)

Comparative Example 2

An electronic endoscope was produced in the same manner as in Comparative Example 1, except that the filament was changed to a carbon fiber.

Further, the carbon fiber used had a softening point of 1,100° C. and the filament had an elongation ratio of lower than 10%.

Comparative Example 3

An electronic endoscope was produced in the same manner as in Comparative Example 1, except that the filament was changed to a silk thread.

Further, the silk thread used was decomposed at a temperature of 150° C. and the filament had an elongation ratio of 10% or higher.

The constitution of the tightening string used in each of the Examples 1 to 4 and the Comparative Examples 1 to 3 is shown in Table 1.

2. Evaluation
2.1 Evaluation of External Appearance

For each of the fifteen electronic endoscopes manufactured in each of the Examples 1 to 4 and the Comparative Examples 1 to 3, an operation of bending the bendable portion tightened by the tightening string was conducted 10,000 times. Then, the external appearance of the region tightened by the tightening string (tightened region) was observed. The observation results of the external appearance were evaluated in accordance with the following four criteria.
A: No fluff found
B: Fluffs found a little but unnoticeable
C: Fluffs found conspicuously
D: A great number of fluffs found 2.2 Evaluation of Post-Cleansing Residues Initially, for each of the fifteen electronic endoscopes manufactured in each of the Examples 1 to 4 and the Comparative Examples 1 to 3 which had been actually used for patients, the region tightened by the tightening string was cleaned with flowing water. Then, the surface of the tightened region was wiped away with a sterilized cotton swab.

Then, an ATP measuring method (stipulated in JIS L 1902) was used to evaluate the ATP relative light level (unit: RLU) which is proportional to the concentration of the residues (*bacillus* or the like) adhering to the cotton swab employed in the wiping process. The results of the evaluation of the ATP relative light level were evaluated in accordance with the following three criteria.

A: 150 RLU or less
B: 151-300 RLU
C: 301 RLU or more 2.3 Evaluation of Chemical Resistance First of all, for each of the fifteen electronic endoscopes manufactured in each of the Examples 1 to 4 and the Comparative Examples 1 to 3, the region tightened by the tightening string was immersed into chemical solution according to the following immersion test conditions.

Immersion Test A
  Ingredient of Chemical Solution: glutaraldehyde
  Content of Ingredient: 3%
  Time Immersed: 60 minutes
  Test Cycle: 5,000
  Number of Piece Tested: 5
Immersion Test B
  Ingredient of Chemical Solution: acetyl hydroperoxide
  Content of Ingredient: 0.3%
  Time Immersed: 30 minutes
  Test Cycle: 5,000
  Number of Piece Tested: 5
Immersion Test C
  Ingredient of Chemical Solution: hydrogen peroxide
  Content of Ingredient: 30%
  Time Immersed: 60 minutes
  Test Cycle: 5,000
  Number of Piece Tested: 5

Subsequently, for each of the respective electronic endoscopes which have undergone the immersion tests, the bendable portion was caused to bend by gradually rotating the operating knob until the magnitude of the angular force applied is increased from the practical use range to the out-of-practical use range.

Then, for the respective electronic endoscopes which have undergone the bending operation, observation was made as to whether the adhesive agent that covers the tightening string was peeled off or not to know the chemical resistance. The observation results were evaluated in accordance with the following three criteria.

A: No peeling of the adhesive agent appears under the bending test even in the out-of-practical use range.

B: The adhesive agent is kept intact within the practical use range but peeled off in the out-of-practical use range.

C: The adhesive agent is peeled off under the bending test within the practical use range.

The results of the evaluations made in the above items 2.1 through 2.3 are shown in Table 1.

TABLE 1

| | Constitution of Tightening String | | | | | | | |
|---|---|---|---|---|---|---|---|---|
| | Filament(mono-filament) | | | | | Filament Twist(multi-filament) | | |
| | Constituent Material | Polar Structure | Softening Point (Melting Point) [°C.] | Elongation Ratio | Outer Diameter [mm] | Number of Filament | Number of Twisting (Primary Twisting) [Tm] | Outer Diameter [mm] |
| Example 1 | Nylon6 | —CONH— | 210 | 10% or higher | 0.008 | 5 | 1000 | 0.04 |
| Example 2 | Vinylon | —OH | 220 | 10% or higher | 0.008 | 5 | 1000 | 0.04 |
| Example 3 | Polyester | —COO— | 240 | 10% or higher | 0.008 | 5 | 1000 | 0.04 |
| Example 4 | Polyurethane | —NHCOO— | 200 | 10% or higher | 0.008 | 5 | 1000 | 0.04 |
| Comp. Ex. 1 | Nylon6 | —CONH— | 210 | 10% or higher | 0.08 | 1 | — | — |
| Comp. Ex. 2 | Carbon Fibers | None | 1100 | under 10% | 0.08 | 1 | — | — |
| Comp. Ex. 3 | Silk Thread | —CONH— | (150) | 10% or higher | 0.08 | 1 | — | — |

| | Constitution of Tightening String Filament Assembly | | | Evaluation Results | | | | |
|---|---|---|---|---|---|---|---|---|
| | Number of Twisting | | | | | Chemical Resistance | | |
| | Number of Filament Twist | (Secondary Twisting) [Tm] | Outer Diameter [mm] | Appearance | Residue | Immersion Test A | Immersion Test B | Immersion Test C |
| Example 1 | 2 | 600 | 0.08 | A | B | B | B | B |
| Example 2 | 2 | 600 | 0.08 | A | B | B | B | B |
| Example 3 | 2 | 600 | 0.08 | A | B | B | B | B |
| Example 4 | 2 | 600 | 0.08 | A | B | B | B | B |
| Comp. Ex. 1 | — | — | — | A | B | C | C | C |
| Comp. Ex. 2 | — | — | — | C | D | C | C | C |
| Comp. Ex. 3 | — | — | — | C | D | D | D | D |

*( )means that the constituent material was decomposed

As is apparent from Table 1, in the case of the electronic endoscopes produced in each of the Examples 1 to 4, the region tightened by the tightening string had an excellent external appearance with no fluff. Presumably, this is because the filaments of the tightening string have elongatability and relieve the tensile force generated by the bending operation of the electronic endoscope, thus keeping the filaments from severing.

In contrast, in each of the Comparative Examples 1 to 3, the filament was partly severed and fluffs were found at the region tightened by the tightening string comprised of a carbon fiber and a silk thread other than a synthetic resin.

Further, in case of the electronic endoscopes produced in each of the Examples 1 to 4, it could be seen that the ATP relative light level was reduced to no greater than 150 RLU and the post-cleansing concentration of the residues (*bacillus* or the like) adhering to the tightened region was low enough. Presumably, this is because the tightening string is made of a synthetic resin, thus making it difficult for the fluffs to be created in the tightening string and, further because the surface of the tightening string exhibits increased smoothness, thereby making it difficult for the *bacillus* or the like to stay on the surface of the tightening string and also making it possible for the *bacillus* or the like to be easily removed by cleansing.

In contrast, it has been clearly confirmed that, in the electronic endoscopes of the Comparative Examples 2 and 3, the ATP relative light level was increased to 151 RLU or more and the concentration of the residues was kept high. Presumably, this is because the tightening string (filament) is severed into fluffs and the adhesive agent is peeled of f in the electronic endoscopes of the Comparative Examples 2 and 3, thereby making it easy for the *bacillus* or the like to stay on the surface of the tightening string and hence making it difficult for the *bacillus* or the like to be removed by water flow cleansing.

Moreover, the tightened region of the electronic endoscopes produced in each of the respective Examples has exhibited high durability against the chemical solution of superior disinfectability and strong sterilizing property, such as glutaraldehyde, acetyl hydroperoxide and hydrogen peroxide.

In contrast, the tightened region of the electronic endoscopes produced in each of the Comparative Examples 1 to 3 was degraded by the chemical solution, and the adhesive agent was peeled off from the tightened region by the bending operation with a force in the out-of-practical use range.

Next, fourth to seventh embodiments of a tightening string for an endoscope according to the present invention will be explained with reference to FIG. 7 to FIG. 11.

<Fourth Embodiment>

Initially, description will be made with regard to a fourth embodiment of a tightening string for an endoscope according to the present invention.

Figure 8:
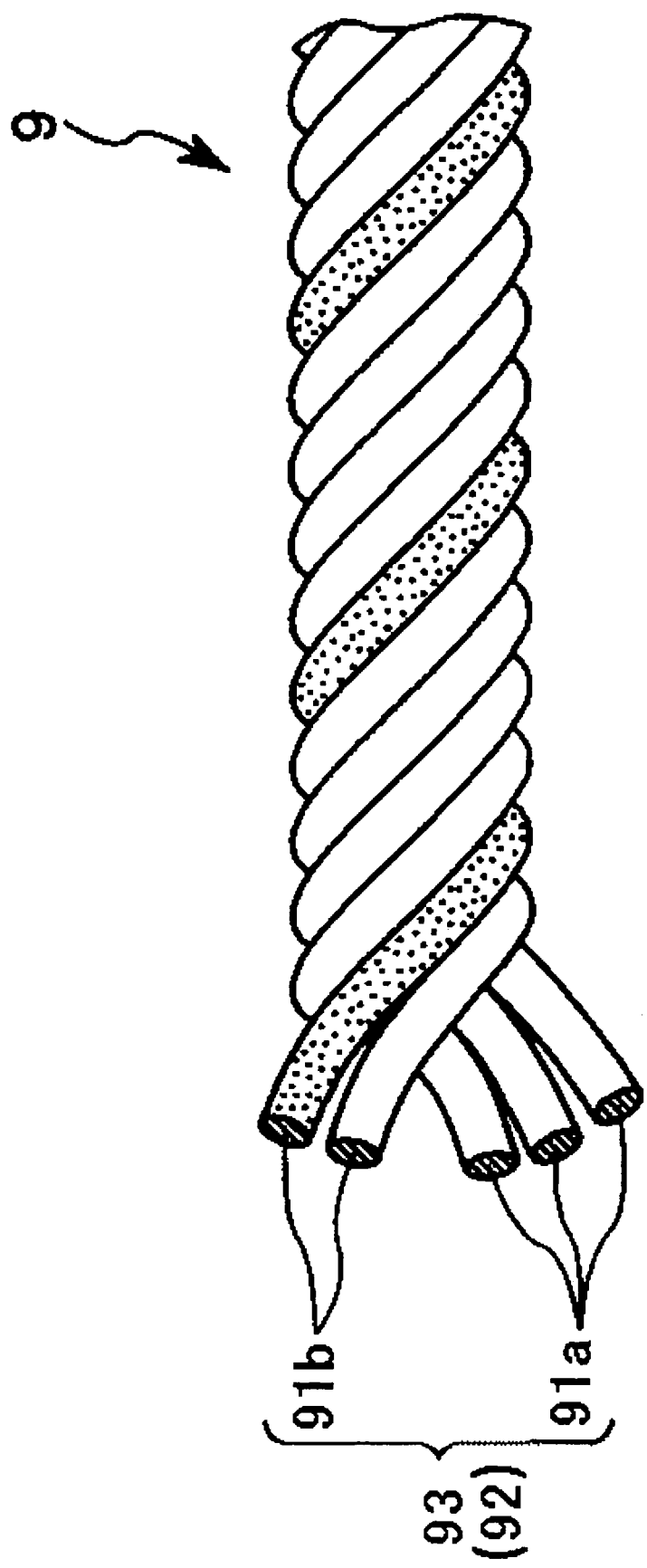
FIG. 8 is a perspective view of the fourth embodiment of a tightening string for an endoscope in accordance with the present invention.

FIG. 8 is a perspective view showing the fourth embodiment of the tightening string for an endoscope in accordance with the present invention.

The tightening string 9 shown in FIG. 8 is constituted from a filament assembly 93 which is comprised of a filament twist 92 obtained by twisting four first filaments 91*a* and one second filament 91*b*. Use of this tightening string 9 makes it possible to secure the outer cover 32 and the outer cover 42 more reliably. Further, a stronger anchor effect can be obtained between the adhesive agent 94 and the tightening string 9 for an endoscope.

In this tightening string 9, each of the first filaments 91*a* has an elongation ratio of 10% or less.

The outer diameter of the first filament 91*a* is preferably in the range of 0.005 to 0.01 mm, and more preferably in the range of 0.003 to 0.02 mm. Since the first filament 91*a* has such a relatively small diameter, it is possible to adjust the outer diameter of the tightening string 9 precisely and easily by changing the number of the first filament 91*a*.

Further, since it is possible to bundle many thin first filaments 91*a* with the second filament 91*b* when the tightening string 9 is formed, it is possible to increase a surface area of the tightening string 9, thereby enabling to enhance the anchor effect by the adhesive agent 94 further.

In this tightening string 9, a tensile strength of the first filament 91*a* is preferably 20 g/denier or higher, and more preferably 25 g/denier or higher. As used herein, "denier" means a unit representing the fineness of a yarn, and 1 denier represents the outer diameter of a yarn whose length is 9,000 m and whose mass is 1 g, whereas 1 tex represents the outer diameter of a yarn whose length is 1,000 m and whose mass is 1 g.

Further, it is preferred that the first filament 91*a* is formed of a resin material. Since such a filament formed of a resin material is a pliant yarn, it is difficult to be severed when tightening the outer cover 32 and the outer cover 42.

In this case, it is preferred that the synthetic resin has polar structures in its main chains and/or side chains. This strengthens the interaction between the polar structures and the adhesive agent 94 and thus can enhance the bonding strength between the first filaments 91*a* and the adhesive agent 94.

The synthetic resin may include, as the polar structures, at least one of —OH, —CHO, —NCO, —COOH, —NO$_2$, —NH$_2$, —SH, —SO$_3$H, —CN, —O—, —CO—, —COO—, —CONH—, —CONHCO—, —NHCOO— and —S—. In this regard, it is preferred that the synthetic resin include, as the polar structures, at least one of —OH, —CHO, —NCO, —COOH, —O—, —CO—, —COO—, —CONH—, —CONHCO— and —NHCOO—. These polar structures are contained in great quantity within a constituent material of the adhesive agent 94. Therefore, by permitting the main chains and/or side chains to contain the polar structures, it becomes possible to make greater the bonding strength between the filaments 91*a* and the adhesive agent 94.

Furthermore, among these resin materials, a resin material mainly formed of a polyarylate-based resin is preferably used. Since the polyarylate-based resin has an elongation ratio at room temperature of 10% or less and has excellent tensile strength, it is possible to obtain a tightening string 9 for an endoscope which is difficult to sever and by which it is possible to tighten the outer cover 32 and the outer cover 42 firmly. Here, the term room temperature means 20° C., for example. Further, the polyarylate-based resin also has high elasticity. Therefore, by tightening the outer cover 32 and the outer cover 42 with tensioning the tightening string 9, the tightening string 9 is contracted after tightening it, and thus this provides a more firmly tightening state.

Such a first filament 91*a* may be obtained by untwisting (sleave) a multifilament such as a machine-sewing yarn or sewing yarn or the like.

On the other hand, the second filament 91*b* is a filament having an elongation ratio at room temperature is 10% or more. An outer diameter of the second filament 91*b* is preferably in the range of 0.003 to 0.02 mm, and more preferably in the range of 0.005 to 0.01 mm. Since the second filament 91*b* also has such a relatively small diameter, it is possible to adjust the outer diameter of the tightening string 9 precisely and increase an outer surface area of the tightening string 9 to thereby enhance the anchor effect by the adhesive, in the same manner as the first filament 91*a*.

In this tightening string 9, a tensile strength of the second filament 91*b* is preferably 20 g/denier or lower, and more preferably 10 g/denier or lower.

Further, it is preferred that the second filament 91*b* is formed of a material having an elongation breaking at room temperature of 10% or higher. For example, it is preferred that the second filament 91*b* is mainly formed of a resin material or mainly formed of a metallic material. This makes it possible to easily obtain a filament 91*b* having an elongation ratio at room temperature of 10% or higher.

Specific examples of the resin material include: polyamide-based resin such as nylon 6, nylon 66, nylon 612 and aramid; polyphenylene sulfide-based resin; polyurethane-based resin; polyester-based resin such as polyethylene terephthalate and polybutylene terephthalate; and acryl-based resin such as polymethylmethacrylate, polyethylmethacrylate, methacrylic ester and acrylic acid ester. One of these resins may be used independently or two or more of these resins may be used in combination.

Among these resin materials, a resin material containing as its main component one of a polyamide-based rein or polyphenylene sulfide-based resin. Since these resins have an elongation ratio at room temperature of 10% or higher, they have a sufficient tensile strength for tightening the outer cover 32 and the outer cover 42 reliably.

In the same manner as the first filament 91a described above, the second filament 91b may be obtained by untwisting (sleaving) a multifilament such as a machine-sewing yarn or sewing yarn or the like.

Further, examples of the metallic material include stainless steel, tungsten, molybdenum, copper, brass, nickel, and the like. One of these metallic materials may be used independently or two or more of these metallic materials may be used in combination.

Among these metallic materials, a metallic material containing as its main component one of stainless steel or tungsten. By using these metallic materials, it is possible to easily obtain a relatively fine filament having an elongation ratio at room temperature of 10% or higher though there is an exception depending on the shape thereof (e.g. the outer diameter of the filament) or the like. Further, since these metallic materials have an extremely high hardness, it is possible to prevent the tightening string 9 from being severed due to abrasion caused by friction when tightening the outer cover 32 and the outer cover 42.

Further, it is also preferred that the constituent material of the first filament 91a and the constituent material of the second filament 91b have a melting point or softening point of 150° C. or higher, and more preferably 170° C. or higher. This makes it possible for the tightening string 9 to have sufficient resistance against a disinfecting or sterilizing treatment conducted in an autoclave or the like under an elevated temperature. As a result, even though the electronic endoscope 1 is repeatedly subject to a sterilizing treatment (particularly, an autoclave sterilization), it is possible to keep high the liquid-tightness between the flexible tubular portion 3 and the bendable portion 4 reliably for a prolonged period of time.

In this regard, it goes without saying that it is preferred that the constituent material of the first filament 91a and the constituent material of the second filament 91b will not be subject to dissolution, hydrolytic cleavage, shrinkage, and deformation, and the like when such a sterilizing treatment is carried out.

Furthermore, when an elongation ratio at room temperature of the first filament 91a is defined by $S_1$ [%] and an elongation ratio at room temperature of the second filament 91b is defined by $S_2$ [%], the value of $S_1/S_2$ is preferably in the range of about 0.02 to 0.94, and more preferably in the range of about 0.1 to 0.7. This makes it possible to tighten the outer cover 32 and the outer cover 42 firmly with the tightening string 9 while reliably preventing the outer cover 32 and the outer cover 42 from being damaged due to the tightening by exhibiting an appropriate elongation.

In this regard, it is to be noted that in the case where two ore more kinds of constituent materials are used as the constituent material of each of the first filament 91a and second filament 91b and thereby two or more elongation ratios can be found in each of the first filament 91a and second filament 91b, an average value of the elongation ratios of the first filament 91a and an average value of the elongation ratios of the second filament 91b are defined as $S_1$ and $S_2$, respectively.

The filament twist 92 is produced by twisting the first filaments 91a and the second filament 91b as described above. At this time, the number of twisting may preferably be, but is not particularly limited to, about 700 to 1,500 T/m, and more preferably about 800 to 1,200 T/m. As a result of this, it is possible to reliably secure the outer cover 32 and the outer cover 42 with the tightening string 9. Further, a stronger anchor effect is caused between the adhesive and the tightening string 9. In this regard, it should be appreciated that the number of twisting may be increased over the above range, but at that time further effect caused by the number of twisting can not be expected since a strong tensile force is generated in each of the filament 91a and the filament 91b so that they are likely to be severed depending on the constituent materials thereof.

Further, it should be also appreciated that there is no particular restriction in the direction of twist of the filament twist 92.

Further, although the filament twist 92 may be obtained by merely twisting the first filaments 91a and the second filament 91b, it is preferred that the filaments 91a and 91b are bonded (fixed) to one another at least partially along a longitudinal direction thereof. This makes it possible to increase binding strength of the filaments 91a and 91b, and therefore the tightening string 9 maintain a securing condition of the outer cover 32 and the outer cover 43 for an extended period of time and in a stabilized manner.

Examples of the method for affixing the filaments 91a and 91b to one another include a method for applying heat, a method using an adhesive, and a method using fusion bonding (e.g., thermal fusion bonding, ultrasonic fusion bonding and high-frequency fusion bonding).

Among these methods, a method applying heat is particularly preferably used in the case where at leas one of the first filaments 91a and the second filament 91b is formed of a resin material. This method can be carried out as follows, for example.

At first, the first filaments 91a and the second filament 91b are twisted to obtain a filament twist 92.

Then, the filament twist 92 is heated either in a wet atmosphere or in a dry atmosphere. This induces rearrangement of the inter-molecular bonds in the resin material of either of the first filaments 91a or the second filament 91b. As a result, the bonding state of the molecules become stable under the condition that they are twisted, and therefore the first filaments 91a and the second filament 91b are intertwisted to each other so that the are partially fixed to each other along a longitudinal direction thereof.

In this process, the heating temperature is preferably in the range of about 100 to 200° C.

Further, during the heating process, the filament twist 92 can be stably fixed in a more reliable manner by applying a pressing force and/or a tensile force to the filament twist 92.

The filament assembly 93 includes the filament twist 92, and in this embodiment the filament twist 92 is formed from a single filament twist.

The outer diameter of the filament assembly 93 is preferably in the range of 0.05 to 0.15 mm, and more preferably in the range of 0.075 to 0.125 mm, though this is somewhat changed depending on the outer diameter of each of the first filament 91a and the second filament 91b and the number of twisting and the like. In the case where the outer diameter of the filament assembly 93 is within the above mentioned range, it is possible to constitute the tightening string having a sufficient strength using the filament assembly 93 without unnecessarily increasing the outer diameter of the insertion section flexible tube 2.

Further, when the cross-sectional area of the second filament 91b is defined as A [$mm^2$] and the cross-sectional area of the filament assembly 93 is defined as B [$mm^2$], the value A/B is preferably in the range of about 0.05 to 0.5, and more preferably in the range of about 0.2 to 0.5. This makes it possible to firmly tighten the outer cover 32 and the outer cover 42 with the first filaments 91a having a relatively small elongation ratio and to prevent the outer cover 32 and the outer cover 42 from being damaged due to elongation of the second filament 91b having a relatively large elongation ratio, and these synergistic effect becomes conspicuous. That is, by twisting the first filaments 91a and the second filament 91b so as to have the value A/B within the above range, the maximum synergistic effect by the both filaments can be obtained. Further, as stated in the above, it is possible to prevent the outer cover 32 and the outer cover 42 from being damaged. As a result, even though the electronic endoscope 1 is repeatedly subject to a sterilizing treatment (particularly, an autoclave sterilization), it is possible to keep high the liquid-tightness between the flexible tubular portion 3 and the bendable portion 4 reliably for a prolonged period of time.

Furthermore, when the outer diameter of the filament assembly 93 is defined as C [mm], and the average thickness of the outer cover 32 and the outer cover 42 is defined as D [mm], the value C/D is preferably in the range of about 0.05 to 0.5, and more preferably in the range of about 0.1 to 0.3. This makes it possible to increase pain of a patient by an increased diameter of the insertion section flexible tube 2 due to the tightening string while the outer cover 32 and the outer cover 42 are reliably tightened by the tightening string 9.

<Fifth Embodiment>

In the next place, description will be given with regard to a fifth embodiment of a tightening string for an endoscope according to the present invention.

Figure 9:
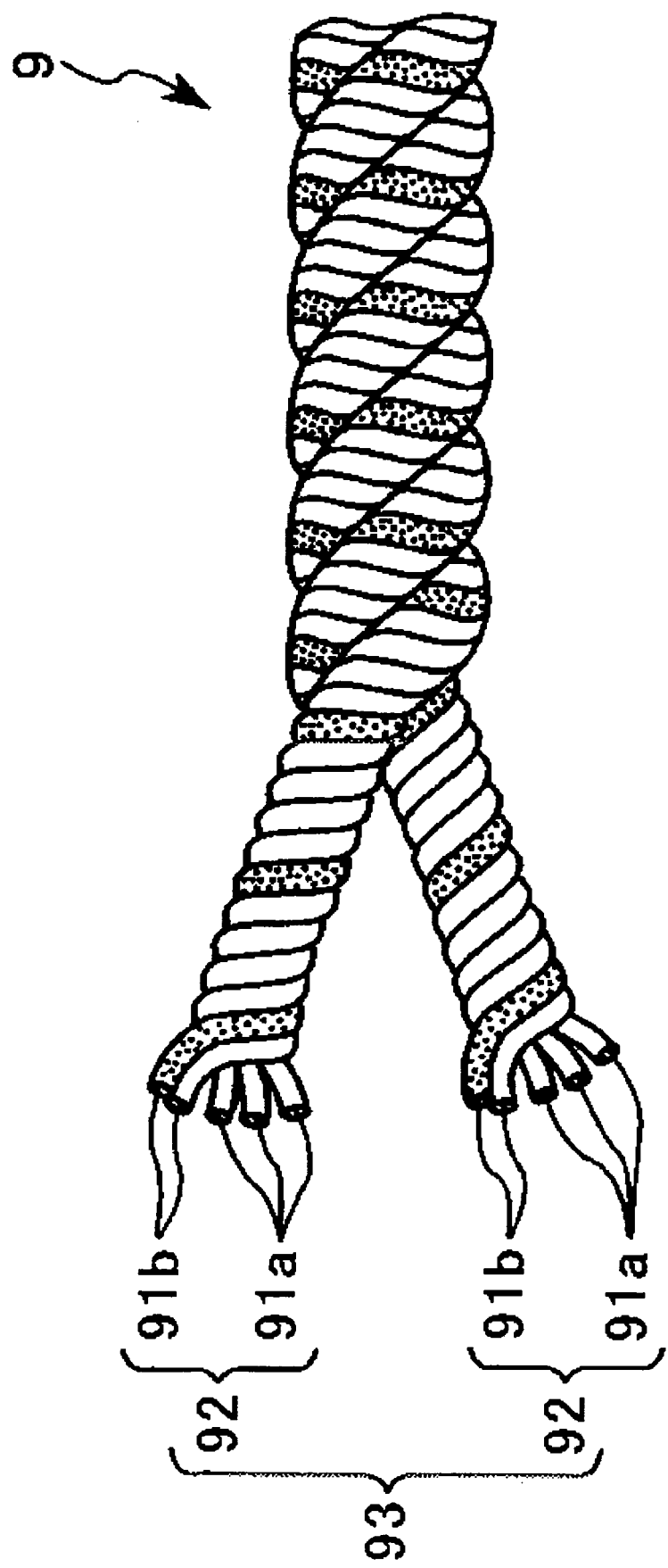
FIG. 9 is a perspective view of the fifth embodiment of a tightening string for an endoscope in accordance with the present invention.

FIG. 9 is a perspective view showing the fifth embodiment of a tightening string for an endoscope in accordance with the present invention.

The following description for the fifth embodiment will be focused on the points differing from the fourth embodiment, and no description will be offered regarding the same matters as in the fourth embodiment.

The tightening string 9 for an endoscope of this fifth embodiment is the same as the fourth embodiment except that the tightening string 9 is constituted from a filament assembly 93 formed by twisting a plurality of filament twists 92. In this regard, FIG. 9 shows a case that two filament twists 92 are twisted as one example of this embodiment.

The outer diameter of each filament twist 92 may preferably be, but is not particularly limited to, in the range of about 0.01 to 0.075 mm, and more preferably in the range of about 0.025 to 0.070 mm.

This filament assembly 93 is produced by bundling a plurality of filament twists 92 together and twisting the same. At this time, the number of twisting may preferably be, but is not particularly limited to, about 400 to 800 T/m, and more preferably about 500 to 700 T/m. The tightening string 9 made from such a filament assembly 9 can reliably secure the outer cover 32 and the outer cover 42. Further, a stronger anchor effect can be created between the adhesive and the tightening string 9.

In this connection, it should be appreciated that there is no particular restriction in the direction of twist of the filament assembly 93. Further, there is also no particular restriction in the direction of twist of each filament twist 93, but it is preferred that these twisting directions are different from each other. By doing so, the twisting of the filament assembly 93 and the twisting of each filament twist are difficult to be untwisted.

The filament assembly 93 may be formed by simply twisting the plurality of filament twists 92, but it is preferred that the filament twists 92 are partially bonded (fixed) to one another at least partially along a longitudinal direction thereof. This makes it possible to prevent the filament twist from being released by its elastic force, so that the twisting of the filament assembly 93 can be maintained for a long period of time in a stable manner.

The partial fixing of the filament twists 92 can be carried out in the same manner as the fixing between the first filament 91a and the second filaments 91b of the fourth embodiment.

According to the tightening string 9 of the fifth embodiment as described above, it is possible to obtain the same functions and effects as those in the fourth embodiment.

Namely, since the filament assembly 93 is constituted by twisting the plurality of filament twists 92, a plurality of ridges-and-valleys are created on the surface of the filament assembly 93, thus greatly increasing the surface area of the filament assembly 93. This enables an anchor effect to be exhibited particularly strongly, thereby making it possible for the adhesive agent 94 to quite reliably secure the tightening string 9 in place. It is also possible to improve the mechanical strength of the tightening string 9 as a whole.

<Sixth Embodiment>

In the next place, description will be given with regard to a seventh embodiment of a tightening string for an endoscope according to the present invention.

Figure 10:
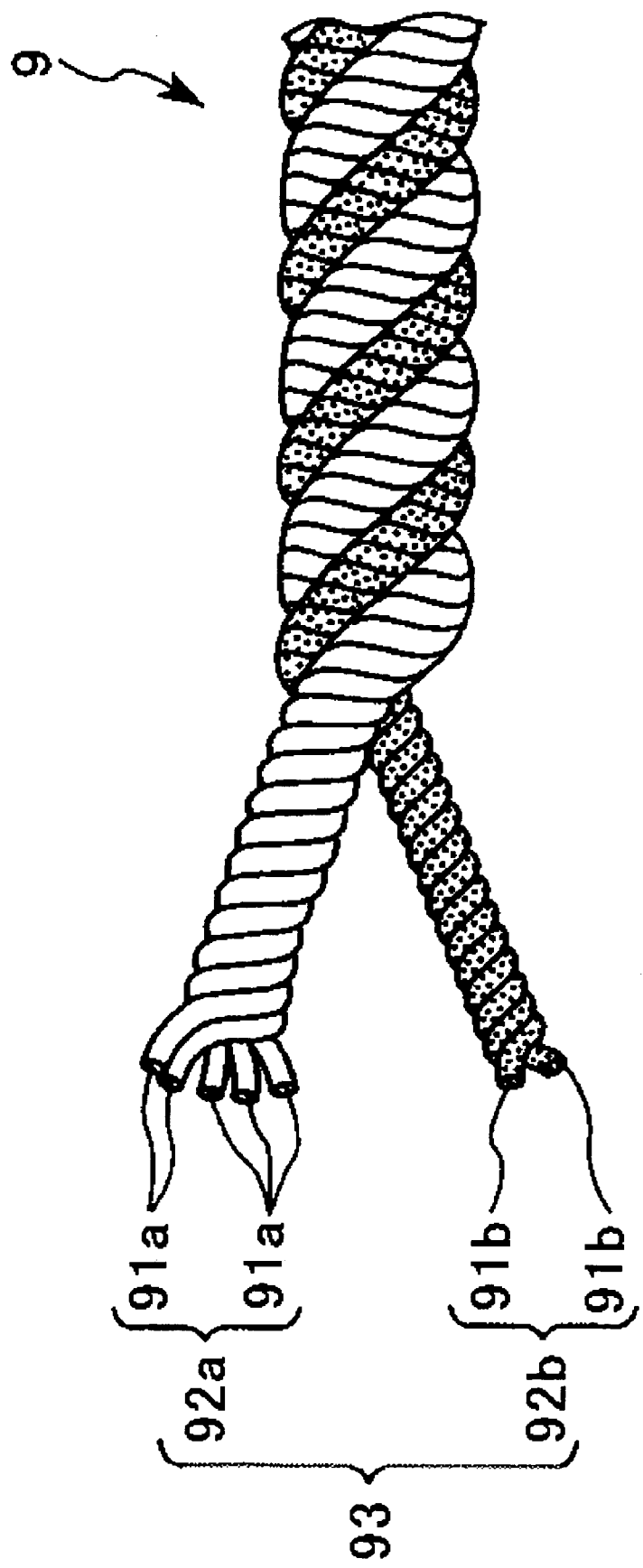
FIG. 10 is a perspective view of the sixth embodiment of a tightening string for an endoscope in accordance with the present invention.

FIG. 10 is a perspective view showing the sixth embodiment of a tightening string for an endoscope in accordance with the present invention.

The following description for the sixth embodiment will be focused on the points differing from the fourth and fifth embodiments, and no description will be offered regarding the same matters as in the fourth and fifth embodiments.

The tightening string 9 for an endoscope of this sixth embodiment is the same as the fourth embodiment except that the tightening string 9 is constituted from a filament assembly 93 which is formed by twisting a first filament twist 92a obtained by twisting a plurality of first filaments 91a and a second filament twist 92b obtained by twisting a plurality of second filaments 91b. In this regard, FIG. 10 shows a case that a first filament twist 92a obtained by twisting five first filaments 91a and a second filament twist 92b obtained by twisting five filaments 91b are twisted together to form a filament assembly 93.

As described above, in this example, the first filament twist 92a is formed only by twisting a plurality of first filaments 91a and the second filament twist 92b is formed only by twisting a plurality of second filaments 91b. Therefore, as compared to the case where first filaments 91a and second filaments 92 are twisted, it is possible to save a time for producing each filament twist.

Further, the outer diameter, the number of twisting, and the direction of twisting of the first filament twist 92a are the same as those of the second filament twist 92b.

According to the tightening string 9 of the sixth embodiment as described above, it is possible to obtain the same functions and effects as those in the fourth and fifth embodiments.

<Seventh Embodiment>

In the next place, description will be given with regard to a seventh embodiment of a tightening string for an endoscope according to the present invention.

Figure 11:
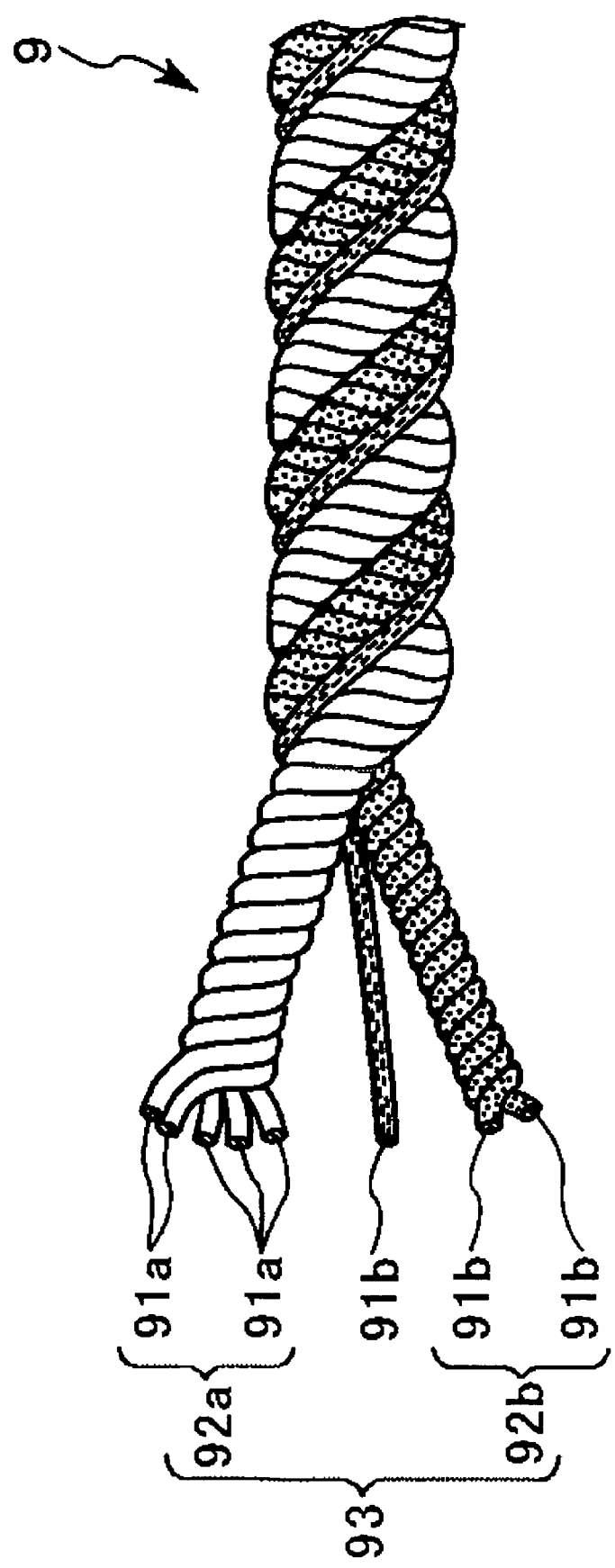
FIG. 11 is a perspective view of the seventh embodiment of a tightening string for an endoscope in accordance with the present invention.

FIG. 11 is a perspective view showing the seventh embodiment of a tightening string for an endoscope in accordance with the present invention.

The following description for the seventh embodiment will be focused on the points differing from the fourth to sixth embodiments, and no description will be offered regarding the same matters as in the fourth to sixth embodiments.

The tightening string 9 for an endoscope of this seventh embodiment is the same as the fourth embodiment except that the tightening string 9 is constituted from a filament assembly 93 which is formed by twisting one or more first filament twists 92a, one or more second filament twists 92b, and one or more second filaments 91b. In this regard, FIG. 11 shows a case that a first filament twist 92a obtained by twisting five first filaments 91a, a second filament twist 92b obtained by twisting two second filaments 91b, and one second filament 91b are twisted together to form a filament assembly 93.

In this case, as a constituent material of the second filament 91b, a metallic material can be used. This makes it possible to improve abrasion resistance of the obtained tightening string 9.

According to the tightening string 9 of the seventh embodiment as described above, it is possible to obtain the same functions and effects as those in the fourth to sixth embodiments.

Further, in the tightening string 9 according to the present invention, it is possible to arbitrarily use two or more of the fourth to seventh (or the first to seventh) embodiments in combination.

For example, the tightening string 9 may be comprised of a filament assembly 93 formed by combining one or more filament twists 92 and one or more of first filaments 91a and second filaments 91b.

Furthermore, in the tightening string 9 according to the present invention, it is not necessary that the filament assembly 93 is formed of a synthetic resin, and other materials may be used for the filament assembly.

Practical Examples

Hereinbelow, practical examples of the present invention employing the tightening strings of the fourth to seventh embodiments described above will be described in more detail.

1. Production of Electronic Endoscope

Example 1

Initially, a rigid portion, a bendable portion and a flexible tubular portion for the endoscope shown in FIG. 1 were prepared (using the components of Endoscope FB-29X manufactured by Pentax Corporation, Japan).

Then, the base end of the rigid portion was inserted into and affixed to the tip end of an outer cover of the bendable portion, and the tip end of a core member of the flexible tubular portion was inserted into and affixed to the base end of an outer cover of the bendable portion.

Subsequently, a tightening string for an endoscope was prepared.

The tightening string was constituted from a filament assembly obtained by twisting four first filaments and one second filament. The details of the constitution of the tightening string were as follow. In this regard, the elongation ratio (breaking elongation ratio) of a filament was a value measured by Autograph (a product of Shimazu Corporation, Japan). Hereinbelow, the term "room temperature" means 20° C., for example.

Constitution of Tightening String
  First Filament (hereinafter, simply referred to as "F1")
    Constituent Material: polyarylate (obtained by untwisting "Vectran" which is a product name of KURARAY Co., Ltd.)
    Softening Point: 175° C.
    Elongation Ratio (at room temperature): 10% or lower
    Outer Diameter: 0.006 mm
  Second Filament (hereinafter, simply referred to as "F2")
    Constituent Material: polyphenylene sulfide (obtained by untwisting "PROCON" which is a product name of TOYOBO C., Ltd.)
    Softening Point: 260° C.
    Elongation Ratio (at room temperature): 10% or higher
    Outer Diameter: 0.01 mm
  Filament Assembly (Tightening String)
    Number of Filament F1: 4
    Number of Filament F2: 1
    Number of Twisting: 940 T/m
    Outer Diameter (C): 0.034 mm
    Cross-section of F2 (A): $7.9 \times 10^{-5}$ mm$^2$
    Cross-section (B): $1.9 \times 10^{-4}$ mm$^2$ Then, the tip end of the outer cover of the bendable portion, the base end of the outer cover of the bendable portion, and the tip end of the outer cover of the flexible tubular portion were tightened by the tightening string thus produced. Then, an adhesive agent mainly composed of epoxy-based resin was supplied in such a manner as to cover the tightening string. Thereafter, the adhesive agent was heated at a temperature of 85° C. for one hour to cure the same, thus securing the tightening string in place.

Subsequently, an electronic endoscope was manufactured using the bonded body (that is, the insertion section of an endoscope) thus obtained. The details of the constitution of the respective portions were as follows.

Rigid Portion
  Constituent Material: aluminum alloy
  Shape: cylindrical, with three varying outer diameters
  Outer Diameter of Intermediate Part: 9 mm
Bendable Portion
  Dimension of Nodal Ring Assembly: outer diameter of 9 mm and inner diameter of 7 mm
  Constituent Material of Nodal Ring: stainless steel
  Constituent Material of Lattice Tube: stainless steel
  Average Thickness of Outer Cover: outer diameter of 10 mm and inner diameter of 9 mm (average thickness of 500 μm)
  Constituent Material of Outer Cover: fluoro-rubber
Flexible Tubular Portion
  Dimension of Core Member: outer diameter of 9 mm and inner diameter of 7 mm
  Constituent Material of Helical tube: stainless steel
  Constituent Material of Lattice tube: stainless steel
  Dimension of Outer Cover: outer diameter of 10 mm and inner diameter of 9 mm (average thickness of 500 μm)
  Constituent Material of Outer Cover: polyurethane-based thermoplastic elastomer Example 6

An electronic endoscope was produced in the same manner as in Example 5, except that the constituent material of the second filament was changed to nylon 6. The details of the constitution of the second filament were as follows.

Second Filament (F2)
  Constituent Material: nylon 6
  Softening Point: 210° C.
  Elongation Ratio (at room temperature): 10% or higher
  Outer Diameter: 0.01 mm Example 7

An electronic endoscope was produced in the same manner as in Example 5, except that the constituent material of the second filament was changed to tungsten. The details of the constitution of the second filament were as follows.

Second Filament (F2)
  Constituent Material: tungsten
  Melting Point: 3380° C.
  Elongation Ratio (at room temperature): 10% or higher
  Outer Diameter: 0.01 mm

Example 8

An electronic endoscope was produced in the same manner as in Example 5, except that the constituent material of the second filament was changed to stainless steel. The details of the constitution of the respective portions were as follows.
  Second Filament Twist Filament (F2)
    Constituent Material: stainless steel
    Melting Point: 1500° C.
    Elongation Ratio (at room temperature): 10% or higher
    Outer Diameter: 0.01 mm

Example 9

An electronic endoscope was produced in the same manner as in Example 5, except that the tightening string was constituted from a filament assembly obtained by twisting three filaments each of which had been formed by twisting four first filaments and one second filament. The details of the constitution of the tightening string were as follow.
  Constitution of Tightening String
  First Filament (F1)
    Constituent Material: polyarylate (obtained by untwisting "Vectran" which is a product name of KURARAY Co., Ltd.)
    Softening Point: 175° C.
    Elongation Ratio (at room temperature): 10% or lower
    Outer Diameter: 0.006 mm
  Second Filament (F2)
    Constituent Material: polyphenylene sulfide (obtained by untwisting "PROCON" which is a product name of TOYOBO C., Ltd.)
    Softening Point: 260° C.
    Elongation Ratio (at room temperature): 10% or higher
    Outer Diameter: 0.01 mm
  Filament Twist
    Number of First Filament (F1): 4
    Number of Second Filament (F2): 1
    Number of Twisting (lower): 940 T/m
    Outer Diameter: 0.034 mm
  Filament Assembly (Tightening String)
    Number of Filament Twists: 3
    Number of Twisting: 550 T/m
    Outer Diameter (C): 0.09 mm
    Cross-section of F2 (A): $2.4 \times 10^{-4}$ mm$^2$
    Cross-section (B): $5.7 \times 10^{-4}$ mm$^2$

Example 10

An electronic endoscope was produced in the same manner as in Example 5, except that the tightening string was constituted from a filament assembly obtained by twisting two filament twists each of which had been formed by twisting five first filaments and a filament twist which had been formed by twisting two second filaments. The details of the constitution of the tightening string were as follow.
  Constitution of Tightening String
  First Filament (F1)
    Constituent Material: polyarylate (obtained by untwisting "Vectran" which is a product name of KURARAY Co., Ltd.)
    Softening Point: 175° C.
    Elongation Ratio (at room temperature): 10% or lower
    Outer Diameter: 0.006 mm
  Filament Twist of First Filaments (hereinafter, simply referred to as "T1")
    Number of F1: 5
    Number of Twisting (lower): 940 T/m
    Outer Diameter: 0.03 mm
  Second Filament (F2)
    Constituent Material: polyphenylene sulfide (obtained by untwisting "PROCON" which is a product name of TOYOBO C., Ltd.)
    Softening Point: 260° C.
    Elongation Ratio (at room temperature): 10% or higher
    Outer Diameter: 0.01 mm
  Filament Twist of Second Filaments (hereinafter, simply referred to as "T2")
    Number of Second Filament (F2): 2
    Number of Twisting (lower): 940 T/m
    Outer Diameter: 0.02 mm
  Filament Assembly (Tightening String)
    Number of T1: 3
    Number of T2: 1
    Number of Twisting (upper): 550 T/m
    Outer Diameter (C): 0.08 mm
    Cross-section of F2 (A): $1.6 \times 10^{-4}$ mm$^2$
    Cross-section (B): $4.4 \times 10^{-4}$ mm$^2$

Example 11

An electronic endoscope was produced in the same manner as in Example5, except that the tightening string was constituted from a filament assembly obtained by twisting another one second filament was added to the tightening string of Example 10 and they were twisted together. The details of the constitution of the tightening string were as follow.
  Constitution of Tightening String
  First Filament (F1)
    Constituent Material: polyarylate (obtained by untwisting "Vectran" which is a product name of KURARAY Co., Ltd.)
    Softening Point: 175° C.
    Elongation Ratio (at room temperature): 10% or lower
    Outer Diameter: 0.006 mm
  Filament Twist of First Filaments (T1)
    Number of F1: 5
    Number of Twisting (lower): 940 T/m
    Outer Diameter: 0.03 mm
  Second Filament (F2)
    Constituent Material: polyphenylene sulfide (obtained by untwisting "PROCON" which is a product name of TOYOBO C., Ltd.)
    Softening Point: 260° C.
    Elongation Ratio (at room temperature): 10% or higher
    Outer Diameter: 0.01 mm
  Filament Twist of Second Filaments (T2)
    Number of Second Filament (F2): 2
    Number of Twisting (lower): 940 T/m
    Outer Diameter: 0.02 mm
  Another Second Filament (hereinafter, simply referred to as "F2a")
    Constituent Material: tungsten
    Melting Point: 3380° C.
    Elongation Ratio (at room temperature): 10% or higher
    Outer Diameter: 0.01 mm Filament Assembly (Tightening String)
  Number of T1: 2
  Number of T2: 1
  Number of F2a: 1
  Number of Twisting (upper): 550 T/m
  Outer Diameter (C): 0.09 mm
  Cross-section of F2 (A): $1.6 \times 10^{-4}$ mm$^2$
  Cross-section of F2a (A): $7.9 \times 10^{-5}$ mm$^2$
  Cross-section (B): $5.2 \times 10^{-4}$ mm$^2$ Comparative Example 4

An electronic endoscope was produced in the same manner as in Example 5, except that a filament assembly was obtained by twisting three multi filament twisted yarns made of a polyarylate resin ("Vectran" which is a product name of KURARAY Co., Ltd.). The details of the constitution of the tightening string were as follow.
  Constitution of Tightening String
  First Filament (F1)
    Constituent Material: polyarylate ("Vectran" which is a product name of KURARAY Co., Ltd.)
    Softening Point: 175° C.
    Elongation Ratio (at room temperature): 10% or lower
    Outer Diameter: 0.006 mm
  Filament Twist of First Filaments (T1)
    Number of F1: 20
    Number of Twisting (lower): 950 T/m
    Outer Diameter: 0.12 mm
  Filament Assembly (Tightening String)
    Number of T1: 3
    Number of Twisting (upper): 550 T/m
    Outer Diameter: 0.36 mm Comparative Example 5

An electronic endoscope was produced in the same manner as in Example 5, except that a single filament was prepared as a tightening string, the tightening string was used to manufacture the endoscope. The details of the constitution of the tightening string were as follow.
  Constitution of Tightening String
  Filament
    Constituent Material: silk thread
    Elongation Ratio (at room temperature): more than 10%
    Number of Filament: 1
    Outer Diameter: 0.08 mm The constitution of the tightening string used in each of the Examples 5 to 11 and the Comparative Examples 4 and 5 are shown in Table 2.

TABLE 2

| | Constitution of Tightening String | | | | | | | |
|---|---|---|---|---|---|---|---|---|
| | Filament | | | | | | | |
| | First Filament(F1) | | Second Filament(F2) | | Other Second Filament(F2') | | Filament Twist | |
| | Constitutional Material | Elongation Ratio($S_1$) | Constitutional Material | Elongation Ratio($S_2$) | Constitu-tional Material | Elongation Ratio($S_2$) | Number of F1 | Number of F2 |
| Example 5 | PAR | 10% or lower | PPS | more than 10% | — | — | 4 | 1 |
| Example 6 | PAR | 10% or lower | PA6 | more than 10% | — | — | 4 | 1 |
| Example 7 | PAR | 10% or lower | W | more than 10% | — | — | 4 | 1 |
| Example 8 | PAR | 10% or lower | SUS | more than 10% | — | — | 4 | 1 |
| Example 9 | PAR | 10% or lower | PPS | more than 10% | — | — | 4 | 1 |
| Example 10 | PAR | 10% or lower | PPS | more than 10% | — | — | 5 | 2 |
| Example 11 | PAR | 10% or lower | PPS | more than 10% | W | more than 10% | 5 | 2 |
| Comp. Ex. 4 | PAR | 10% or lower | — | — | — | — | 20 | — |
| Comp. Ex. 5 | Silk Thread | more than 10% | — | — | — | — | — | — |

| | Constitution of Tightening String | | | | | |
|---|---|---|---|---|---|---|
| | Filament Assembly | | | | | |
| | Number of Filament Twist | Number of F2' | Outer Diameter(C) [mm] | $S_1/S_2$ | A/B | C/D |
| Example 5 | 1 | — | 0.034 | 0.21 | 0.41 | 0.068 |
| Example 6 | 1 | — | 0.034 | 0.03 | 0.41 | 0.068 |
| Example 7 | 1 | — | 0.034 | 0.12 | 0.41 | 0.068 |
| Example 8 | 1 | — | 0.034 | 0.10 | 0.41 | 0.068 |
| Example 9 | 3 | — | 0.10 | 0.21 | 0.41 | 0.20 |
| Example 10 | (2, 1) | — | 0.08 | 0.21 | 0.36 | 0.16 |
| Example 11 | (2, 1) | 1 | 0.09 | 0.11 | 0.46 | 0.18 |
| Comp. Ex. 4 | 3 | — | 0.36 | — | — | — |
| Comp. Ex. 5 | — | — | — | — | — | — |

\* PAR: Polyalylate
PPS: Polyphenylene Sulfide
PA6: Nylon6
W: Tungsten
SUS: Stainless Steel
\* the value in the parenthesis (,) means the value of (T1, T2)

2. Evaluation 2.1 Evaluation of Wear Resistance

Wear resistance of the tightening string used in each of the Examples 5 to 11 and the Comparative Examples 4 and 5 was tested. The wear resistance test was carried out based on the method stipulated by JIS L1096, and the results thereof were evaluated in accordance with the following four criteria.

A: No problem occurred by the friction larger than the actual use.

B: No problem occurred by the friction smaller than the actual use, but abrasion occurred by the friction larger than the actual use.

C: Wear was slightly caused by the friction smaller than the actual use.

D: Wear was caused by the friction smaller than the actual use.

2.2 Evaluation for External Appearance Upon Tightening

In the manufacturing process of each of the electronic endoscopes of the Examples 5 to 11 and the Comparative Examples 4 and 5, after the outer cover of the insertion section flexible tube had been secured by the respective tightening string, the appearance of the portions of the flexible tube secured by the tightening string (that is, the base portion of the outer cover of the bendable portion and the tip portion of the outer cover of the flexible tube portion) was evaluated with naked eyes. This evaluation was made in accordance with the following four criteria.

A: No damage was found on the outer cover.

B: The outer cover could be secured by the tightening string, but a small damage caused by the tightening string was found on the outer cover.

C: The outer cover could be secured by the tightening string, but a considerable damage caused by the tightening string was found on the outer cover.

D: The outer cover was cut by the tightening string.

2.3 Evaluation for External Appearance Upon Manipulation

In each of the electronic endoscopes produced respectively in the Examples 5 to 11 and the Comparative Examples 4 and 5, the bendable portion was caused to bend by gradually rotating the operating knob until the magnitude of the angular force applied was increased from the practical use range to the out-of-practical use range. Then, for each electronic endoscope after the bending manipulation, observation was made as to whether the adhesive agent that covers the tightening string was peeled off or not (that is, the appearance of the tightened region was observed). The observation results were evaluated in accordance with the following four criteria.

A: No peeling-off of the adhesive was not observed even if the bendable portion was bent over the practical use range.

B: No problem occurred within the practical use range, but the adhesive was peeled off when the bendable portion was bent out of the practical use range.

C: The adhesive was slightly peeled off when the bendable portion was bent within the practical use range.

D: The adhesive was peeled off when the bendable portion was bent within the practical use range.

2.3 Evaluation for Outer Diameter of Tightened Regions

In each of the electronic endoscopes produced respectively in the Examples 5 to 11 and the Comparative Examples 4 and 5, the outer diameter of the tightened region tightened by the tightening string was measured. The results of the measurement were evaluated in accordance with the following three criteria on the assumption that the flexible tubes of the endoscopes having the respective measured outer diameters be inserted into a patient.

A: Outer diameters having no difficulty for insertion.

B: Outer diameters which are insertable, but have difficulty upon insertion.

C: Outer diameters which cannot be inserted.

2.5 Evaluation of Post-Cleansing Residues

In each of the electronic endoscopes of the Examples and the Comparative Examples which had been actually used for patients, the region of the flexible tube tightened by the tightening string was cleaned with flowing water. Then, the surface of the tightened region was wiped away with a sterilized cotton swab. Thereafter, an ATP measuring method (stipulated in JIS L 1902) was used to evaluate the ATP relative light level (unit: RLU) which is proportional to the concentration of the residues (*bacillus* or the like) adhering to the cotton swab employed in the wiping process. The results of such an evaluation of the ATP relative light level were evaluated in accordance with the following three criteria.

A: 150 RLU or less

B: 151 to 300 RLU

C: 301 RLU or more 2.6 Evaluation of Chemical Resistance

First of all, for each of the fifteen electronic endoscopes produced respectively in the Examples and the Comparative Examples, the region tightened by the tightening string was immersed into chemical solution according to the following immersion test conditions.

Immersion Test A
 Ingredient of Chemical Solution: glutaraldehyde
 Content of Ingredient: 3%
 Time Immersed: 30 minutes
 Test Cycle: 5,000
 Number of Endoscope Tested: 5

Immersion Test B
 Ingredient of Chemical Solution: acetyl hydroperoxide (60° C.)
 Content of Ingredient: 0.3%
 Time Immersed: 30 minutes
 Test Cycle: 5,000
 Number of Endoscope Tested: 5

Immersion Test C
 Ingredient of Chemical Solution: hydrogen peroxide
 Content of Ingredient: 30%
 Time Immersed: 60 minutes
 Test Cycle: 5,000
 Number of Endoscope Tested: 5

Subsequently, for the respective electronic endoscopes which have undergone the immersion tests, the bendable portion was caused to bend by gradually rotating the operating knob until the magnitude of the angular force applied is increased from the practical use range to the out-of-practical use range.

Then, for the respective electronic endoscopes which have undergone the bending operation, observation was made as to whether the adhesive agent that covers the tightening string was peeled off or not to know the chemical resistance. The observation results were evaluated in accordance with the following three criteria.

A: No peeling off of the adhesive agent was observed under the bending test even in the out-of-practical use range.

B: The adhesive agent was kept intact within the practical use range but peeled off in the out-of-practical use range.

C: The adhesive agent was peeled off under the bending test within the practical use range.

2.7 Evaluation for Liquid-tightness

For each of the fifteen electronic endoscopes produced respectively in the Examples 7 to 11 and the Comparative Examples 4 and 5, a disinfecting or sterilizing treatment was repeatedly conducted under high temperature in an autoclave. The conditions of the disinfecting or sterilizing treatment were as follows.
Temperature: 120° C.
Time: 10 minutes
Cycle Repeated: 3,000 times In this test, upon every 500 cycles, an image produced by each endoscope was checked to confirm as to whether or not there was any trouble in the functions of the electronic endoscope. The examination results were evaluated in accordance with the following four criteria.
A: No trouble was confirmed even after 3,000 cycles.
B: Any trouble was confirmed after 3,000 cycles.
C: Any trouble was confirmed between 1,500 and 2,500 cycles.
D: Any trouble was confirmed between 0 and 1,000 cycles.

The results of the evaluations made in the above items 2.1 through 2.7 are shown in Table 3.

ther, since each tightening string was composed of extremely thin filaments and it was constituted by twisting filaments having different elongation ratios, the tightening string had a sufficient tensile strength and a tightening property in spite of its extremely thin structure.

Furthermore, in each of the electronic endoscopes manufactured in the Examples, as a result of the evaluation of the post-cleansing residues, it was confirmed that the ATP relative light level was lower than 150 RLU and therefore the condensation of the residues (*bacillus* or the like) was low. Presumably, this is because since the tightening string was formed from pliant and long fibers, any micro-asperity (fluff or fuzz) is hard to be created on the surface of the tightening portion, and therefore the surface of the tightening portion could have a high flatness, so that *bacillus* or the like were difficult to stay thereon and even if they were present they could be easily removed by water flow cleansing.

TABLE 3

| | Evaluation Results | | | | | | | | |
|---|---|---|---|---|---|---|---|---|---|
| | | Appearance | | Outer Diameter of the | | Chemical Resistance | | | |
| | Wear Resistance | Upon Tightening | Upon Operating | Tightening Region | Residue | Immersion Test A | Immersion Test B | Immersion Test C | Liquid-Tightness |
| Example 5 | B | A | B | B | B | A | A | A | B |
| Example 6 | B | B | B | B | B | A | A | A | B |
| Example 7 | A | B | B | B | B | A | A | A | B |
| Example 8 | A | B | B | B | B | A | A | A | B |
| Example 9 | B | A | A | B | B | A | A | A | A |
| Example 10 | B | A | A | B | B | A | A | A | A |
| Example 11 | A | B | A | B | B | A | A | A | A |
| Comp. Ex. 4 | B | B | D | D | B | A | D | D | D |
| Comp. Ex. 5 | B | C | D | B | D | A | D | D | D |

As is evident from Table 3, the wear resistance of each of the tightening strings used in the Examples 7 to 11 was in the level that no problem occurs even if friction over the practical use is added. Presumably, this is because the wear resistance of the entire of the tightening string was increased since the first filament having the elongation ratio of 10% or lower had relatively high wear resistance.

Further, each of the tightening strings used in the Examples 5 to 11 had an excellent appearance upon tightening. Presumably, this is because each tightening string had an appropriate elongation property since it was formed by twisting a plurality of filaments having different elongation ratios. Namely, it is supposed that each tightening string was easily deformed along the shape of the tightened region and it did not bite into the outer cover beyond necessary level so that the outer cover was suppressed to be damaged by the tightening of the tightening string.

Further, it is supposed that due to this elongation property, each endoscope could have the excellent appearance upon manipulation. In other words, it is supposed that due to this elongation property, a tensile stress exerted on the tightening string upon bending operation was moderated to thereby prevent the tightening string from being cut and the adhesive agent from being peeled off.

Further, each of the tightening strings used in the Examples 5 to 11 had a small outer diameter that can be inserted into a body cavity of a patient without any difficulty. This is because in each of the tightening portions of the electronic endoscopes was tightened by the sufficiently thin tightening string. Fur- In contrast, in each of the electronic endoscopes manufactured in the Comparative Example 5, it has been clearly confirmed that the ATP relative light level was increased to 151 RLU or more and the concentration of the residues was kept high. Presumably, this is because the tightening string (filament) was severed into fluffs and the adhesive agent was peeled off in the electronic endoscopes of the Comparative Example 5, thereby making it easy for the *bacillus* or the like to stay on the surface of the tightening string and hence making it difficult for the *bacillus* or the like to be removed by water flow cleansing.

Moreover, the tightened region of the electronic endoscopes produced in each of the respective Examples has exhibited high durability against the chemical solution of superior disinfectability and strong sterilizing property, such as glutaraldehyde, acetyl hydroperoxide and hydrogen peroxide.

In contrast, the tightened region of each of the electronic endoscopes manufactured in the Comparative Examples 4 and 5 was degraded by the chemical solution, and the adhesive agent was peeled off from the tightened region by the bending operation with a force in the out-of-practical use range.

Moreover, in each of the electronic endoscopes manufactured in the Examples 7-11, any trouble could not be found on the functions thereof even if a disinfecting or sterilizing treatment in an autoclave was repeatedly conducted.

In contrast, in each of the electronic endoscopes manufactured in the Comparative Examples 4 and 5, a phenomenon that an image produced by the endoscope was blurred has been confirmed. It is supposed that this phenomenon was caused by loss of cleanness of the imaging element. It is supposed that the cause of the loss of cleanness resulted from that fact that the outer cover was partially cut and water or the like was entered inside the electronic endoscope through the cutout portion upon the disinfecting or sterilizing treatment.

Although a tightening string for an endoscope, an outer cover securing method, a flexible tube for an endoscope, and an endoscope according to the present invention have been described in conjunction with the embodiments shown in the accompany drawings and the practical examples described above, it should be noted that the present invention is not limited to these embodiments and examples.

If needed, a step for an arbitrary purpose may be added to the outer cover securing method.

The outer cover securing method according to the present invention may also be applied to, e.g., such a case that an outer cover of an insertion section flexible tube is secured onto an operating section and a case that an outer cover of a connecting section flexible tube is secured onto an operating section or a light source plug section.

Further, the respective parts of the endoscope may be replaced with other equivalents that can perform the same functions as they do. It is possible to add other parts of arbitrary construction to the endoscope.

The endoscope according to the present invention is not limited to an electronic endoscope but may encompass an optical endoscope (fiberscope). Further, the endoscope according to the present invention is not limited to an endoscope for medical use but may encompass an endoscope for industrial use.

Finally, it is to be understood that the present disclosure relates to the subject matters contained in Japanese Patent Applications No. 2005-089488 (filed on Mar. 25, 2005) and No. 2005-169686 (filed on Jun. 9, 2005) which are expressly incorporated herein by reference in their entireties.

What is claimed is:

1. A flexible tube for an endoscope, the flexible tube configured to be inserted into a body cavity of a patient, the flexible tube comprising:
    a flexible tubular portion including a core member and an outer cover which covers an outer periphery of the core member, the flexible tubular portion having a tip end and a base end;
    a bendable portion provided at the tip end of the flexible tubular portion and including a core member and an outer cover which covers an outer periphery of the core member, the bendable portion having a tip end and a base end;
    a tightening string securing an end portion of the outer cover of the bendable portion at the base end side thereof and an end portion of the outer cover of the flexible tubular portion at the tip end side thereof, onto the core member of the bendable portion or the core member of the flexible tubular portion, the tightening string comprising a filament assembly formed by bundling a plurality of filaments of a synthetic resin in a rectilinearly arranged condition; and
    an adhesive for securing the tightening string on the outer cover,
    wherein, when the outer diameter of each of the filaments is defined as A and the outer diameter of the filament assembly is defined as B, the value B/A is in the range of 2 to 30,
    wherein the tightening string is applied on an endoscope so that the tightening string forms at least two layers of untwisted filaments, and the adhesive is applied to the tightening string to cover the tightening string so that the adhesive infiltrates between the at least two layers to bond the at least two layers and to affix the tightening string to the outer cover.

2. The flexible tube for an endoscope as claimed in claim 1, wherein the filaments are bonded to one another at least at portions of the filaments along a longitudinal direction thereof.

3. The flexible tube for an endoscope as claimed in claim 2, wherein the bonding is performed by heating.

4. The flexible tube for an endoscope as claimed in claim 1, wherein the synthetic resin has a polar structure in at least one of main chains and side chains of the synthetic resin.

5. The flexible tube for an endoscope as claimed in claim 4, wherein the synthetic resin has, as the polar structure, at least one of —OH, —CHO, —NCO, —COOH, —O—, —CO—, —COO—, —CONH—, —CONHCO— and —NHCOO—.

6. The flexible tube for an endoscope as claimed in claim 1, wherein the synthetic resin has a melting point or softening point which is equal to or higher than 150° C.

7. The flexible tube for an endoscope as claimed in claim 1, wherein each of the filaments has an elongation ratio of higher than 10%.

8. The flexible tube for an endoscope according to claim 1, wherein the outer cover is made of a flexible resin material or a rubber material.

9. An endoscope equipped with the flexible tube for an endoscope as defined in claim 1.

* * * * *